(12) United States Patent
Van Nest et al.

(10) Patent No.: US 8,333,980 B2
(45) Date of Patent: *Dec. 18, 2012

(54) METHODS OF MODULATING AN IMMUNE RESPONSE USING IMMUNOSTIMULATORY SEQUENCES AND COMPOSITIONS FOR USE THEREIN

(75) Inventors: Gary Van Nest, Martinez, CA (US); Stephen F. Tuck, Oakland, CA (US); Joseph Eiden, Jr., Danville, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 702 days.

This patent is subject to a terminal disclaimer.

(21) Appl. No.: 12/270,662

(22) Filed: Nov. 13, 2008

(65) Prior Publication Data

US 2009/0148479 A1 Jun. 11, 2009

Related U.S. Application Data

(63) Continuation of application No. 09/642,492, filed on Aug. 18, 2000, now Pat. No. 7,479,285.

(60) Provisional application No. 60/149,768, filed on Aug. 19, 1999.

(51) Int. Cl.
*A61K 47/00* (2006.01)

(52) U.S. Cl. ............. 424/278.1; 424/193.1; 424/196.11; 424/197.11; 424/201.1; 424/202.1; 424/203.1; 424/206.1; 424/208.1; 424/236.1; 424/275.1

(58) Field of Classification Search ........................ None
See application file for complete search history.

(56) References Cited

U.S. PATENT DOCUMENTS

| | | |
|---|---|---|
| 4,458,066 A | 7/1984 | Caruthers et al. |
| 4,650,675 A | 3/1987 | Borel et al. |
| 4,673,574 A | 6/1987 | Anderson |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,391,723 A | 2/1995 | Priest |
| 5,453,496 A | 9/1995 | Caruthers et al. |
| 5,460,831 A | 10/1995 | Kossovsky et al. |
| 5,552,391 A | 9/1996 | Coutts et al. |
| 5,663,153 A | 9/1997 | Hutcherson et al. |
| 5,723,335 A | 3/1998 | Hutcherson et al. |
| 5,849,719 A | 12/1998 | Carson et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,498,148 B1 | 12/2002 | Raz |
| 6,534,062 B2 | 3/2003 | Raz et al. |
| 6,552,006 B2 | 4/2003 | Raz et al. |
| 6,589,940 B1 * | 7/2003 | Raz et al. .................... 514/44 R |
| 6,613,751 B2 | 9/2003 | Raz et al. |
| 7,479,285 B1 | 1/2009 | Van Nest et al. |

FOREIGN PATENT DOCUMENTS

| | | |
|---|---|---|
| AU | 45288/99 A1 | 11/1999 |
| EP | 0 468 520 A2 | 7/1991 |
| EP | 0 468 520 A3 | 7/1991 |
| JP | 10-506265 A | 6/1998 |
| WO | WO-96/02555 A1 | 2/1996 |
| WO | WO-97/28259 A1 | 8/1997 |
| WO | WO-98/16247 A1 | 4/1998 |
| WO | WO-98/18810 A1 | 5/1998 |
| WO | WO-98/37919 A1 | 9/1998 |
| WO | WO-98/40100 A1 | 9/1998 |
| WO | WO-98/52581 A1 | 11/1998 |
| WO | WO-98-52581 C2 | 11/1998 |
| WO | WO-98/52962 A1 | 11/1998 |
| WO | WO-98/55495 A2 | 12/1998 |
| WO | WO-98/55495 A3 | 12/1998 |
| WO | WO-98/55495 C1 | 12/1998 |
| WO | WO-98/55609 A1 | 12/1998 |
| WO | WO-99/11275 A2 | 3/1999 |
| WO | WO-99/11275 A3 | 3/1999 |
| WO | WO-99/11275 C2 | 3/1999 |
| WO | WO-99/30733 A1 | 6/1999 |
| WO | WO-99/33488 A2 | 7/1999 |
| WO | WO-99/33868 A2 | 7/1999 |
| WO | WO-99/51259 A2 | 10/1999 |
| WO | WO-99/51259 A3 | 10/1999 |
| WO | WO-99/58118 A2 | 11/1999 |
| WO | WO-99/58118 A3 | 11/1999 |
| WO | WO-99/62923 A2 | 12/1999 |
| WO | WO-99/62923 A3 | 12/1999 |
| WO | WO-00/54803 A2 | 9/2000 |
| WO | WO-00/54803 A3 | 9/2000 |
| WO | WO-01/00232 A2 | 1/2001 |
| WO | WO-01/00232 A3 | 1/2001 |
| WO | WO-01/12223 A2 | 2/2001 |
| WO | WO-01/22972 A2 | 4/2001 |
| WO | WO-01/22972 A3 | 4/2001 |
| WO | WO-01/22972 C2 | 4/2001 |
| WO | WO-01/22990 A2 | 4/2001 |
| WO | WO-01/22990 A3 | 4/2001 |
| WO | WO-01/35991 A2 | 5/2001 |
| WO | WO-01/35991 A3 | 5/2001 |

OTHER PUBLICATIONS

Johansson et al (Virology, 225:136-144, 1996).*
Agrawal et al. (1986). "Efficient Methods for Attaching Non-radioactive Labels to the 5' Ends of Synthetic Oligodeoxyribonucleotides," *Nucleic Acids Res.* 14:6227-6245.
Ahmeida et al. (1993). "Immunopotentiation Local and Systemic Humoral Immune Responses by ISCOMs, Liposomes and FCA: Role in Protection Against Influenza A in Mice," *Vaccine* 11:1302-1309.

(Continued)

*Primary Examiner* — Patricia A Duffy
(74) *Attorney, Agent, or Firm* — Morrison & Foerster LLP

(57) ABSTRACT

The invention provides methods of modulating an immune response to a second antigen which entail administration of a first antigen and an immunostimulatory polynucleotide. Modulation of the immune response is generally manifested as stimulation of a Th1 response.

35 Claims, 1 Drawing Sheet

OTHER PUBLICATIONS

Albo et al. (1995). "Identification of an RNBA Binding Region Within the N-Terminal Third of the Influenza A Virus Nucleoprotein," *J. Virol.* 69:3799-3806.

Aramaki et al. (1995). "Interferon-γ inductive Effect of Liposomes as an Immunoadjuvant," *Vaccine* 13:1809-1814.

Asanuma at al. (1995). "Cross-protection against Infuenza Virus Infection in Mice Vaccinated by Combined Nasal/Subcutaneous Administration," *Vaccine* 13:3-5.

Atherton at al. (1981). "Synthesis of a 21-Residue Fragment of Human Proinsulin by the Polyamide Solid Phase Method," *Hoppe Seylers Z Physiol. Chem.* 362:833-839.

Ballas et al. (1996). "Induction of NK Activity in Murine and Human Cells by CpG Motifs in Oligodeoxynucleotides and Bacterial DNA," *J. Immunol.* 157:1840-1845.

Benoit, R. at al. (1987). "Peptides: Strategies for Antibody Production and Radioimmunoassays," *In Neuromethods*. A.A. Boulton at al. eds. Humana Press: Clifton, N.J. pp. 43-72.

Bischoff et al. (1987). "Introduction of 5'-Terminal Functional Groups into Synthetic Oligonucleotides for Selective Immobilization," *Anal. Biochem.* 164:336-344.

Blanks et al. (1988). "An Oligodeoxynucleotide Affinity Colulmn For the Isolation of Sequence Specific DNA Binding Proteins," *Nucleic Acids Res.* 16:10283-10299.

Bliss et al. (1996). "IL-12, as an Adjuvant, Promotes a T Helper 1 Cell, but Does not Suppress a T Helper 2 Cell Recall Response," *J. Immunol.* 156:887-894.

Boggs et al. (1997). "Characterization and Modulation of Immune Stimulation by Modified Oligonucleotides," *Antisense and Nucleic Acid Drug Development* 7:461-471.

Borel et al. (1990). "A Novel Technique to Link Either Proteins or Peptides to Gammaglobulin to Construct Tolerogens," *Immunol. Methods* 126:159-168.

Borel et al. (1995). "Food Allergens Transformed Into Tolerogens," *Int. Arch. Allergy Immunol.* 107:264-267.

Borel et al. (1996). "Parenteral and Oral Administation of Tolerogens: Protein-IgG Conjugates," *Ann. N.Y. Acad. Sci.* 778:80-87.

Boujrad et al. (1993). "Inhibition of Hormone-stimulated Steroidogenesis in Cultured Leydig Tumor Cells by a cholesterol-linked Phosphorothioate Oligodeoxynucleotide Antisense to Diazepam-binding Inhibitor," *Proc. Natl. Acad. Sci. USA* 90:5728-5731.

Bousquet et al. (1999). "Molecular Mechanisms of the Adsorption of a Model Protein (Human Serum Albumin) on Poly(Methylidene malonate 2.1.2) Nanoparticles," *Pharm. Res.* 16:141-147.

Branda et al. (1993). "Immune Stimulation by an Antisense Oligomer Complementary to the rev Gene of Hiv-1," *Biochem. Pharmacol.* 45:2037-2043.

Branda et al. (1996). "Amplification of Antibody Production by Phosphorothioate Oligodeoxynucleotides," *J. Lab. Clin. Med.* 128:329-338.

Braun et al. (1988). "Immunogenic Duplex Nucleic Acids are Nuclease Resistant," *J. Immunol.* 141:2084-2089.

Brazolot Millan et al. (1998). "CpG DNA Can Induce Strong Th1 Humoral and Cell-mediated Immune Responses Against Hepatitis B Surface Antigen in Young Mice," *Proc. Natl. Acad. Sci. USA* 95:15553-15558.

Breiteneder et al. (1989). "The Gene Coding for the Major Birch Pollen Allergen Betvl, is highly Homologous to a Pea Disease Resistance Response Gene," *EMBO J.* 8:1935-1938.

Brett et al. (1991). "Human T Cell Recognition of Influenza A Nucleoprotein Specificity and Genetic Restriction of Immunodominant T Helper Cell Epitopes," *J. Immunol.* 147:984-991.

Broide et al. (1998). "Immunostimulatory DNA Sequences Inhibit IL-5, Eosinophilic Inflammation, and Airway Hyperresponsiveness in Mice," *J. Immunol.* 161:7054-7062.

Broide et al. (1999). "DNA-Based Immunization for Asthma," *Int. Arch. Allergy Immunol.* 118:453-456.

Carson et al. (1997). "Oligonucleotide Adjuvants for T helper 1 (Th1)-specific Vaccination," *J. Exp. Med.* 186:1621-1622.

Chace et al. (1997). "Bacterial DNA-Induced NK Cell IFN-γ Production Is Dependent on Macrophage Secretion of IL-12," *Clin. Immunol. and Immunopathol.* 84:185-193.

Chaturvedi et al. (1996). "Stabilization of Triple-stranded Oligonucleotide Complexes: Use of Probes Containing Alternating Phosphodiester and Stereo-uniformed Cationic Phosphoramidate Linkages," *Nucleic Acids Res.* 24:2318-2323.

Chavany et al. (1992). "Polyalkylcyanoacrylate Nanoparticles as Polymeric Carriers for Antisense Oligonucleotides," *Pharm. Res.* 9:441-449.

Chavany et al. (1994). "Adsorption of Oligonucleotides onto Polyisohexylcyanoacrylate Nanoparticles Protects Them Against Nucleases and Increases Their Cellular Uptake," *Pharm. Res.* 11:1370-1378.

Chen et al. (1999). "Enhanced Protection Against a Lethal Influenza Virus Challenge by Immunization With Both Hemagglutinin- and Neuraminindase-expressing DNAs," *Vaccine* 17:653-659.

Chu et al. (1997). "CpG Oligodeoxynucleotides Act as Adjuvant that Switch on T Helper 1 (Th1) Immunity," *J. Exp. Med.* 186:1623-1631.

Chua et al. (1988). "Sequence Analysis of cDNA Coding for a Major House Dust Mite Allergen, Der p 1," *J. Exp. Med.* 167:175-182.

Chua et al. (1990). "Expression of Dermatophagoides Pteronyssinus Allergen, Der p II, in *Escherichia coli* and the Binding Studies with Human IgE," *Int. Arch. Allergy Appl. Immunol.* 91:124-129.

Connolly. (1985). "Chemical Synthesis of Oligonucleotides Containing a Free Sulphydryl Group and Subsequent Attachmentof Thiol Specific Probes," *Nucleic Acids Res.* 13:4485-4502.

Connolly. (1987). "The Synthesis of Oligonucleotides Containing a Primary Amino Group at the 5'-Terminus," *Nucleic Acids Res.* 15:3131-3139.

Cooper et al. (1996). "Effects of Influenza A Nucleoprotein on Polymorphonuclear Neutrophil Function," *J. Inf. Diseases* 173:279-284.

Corey et al. (1987). "Generation of a Hybrid Sequence-Specific Single-Stranded Deoxyribonuclease," *Science* 238:1401-1403.

Cowdery et al. (1996). "Bacterial DNA-Induced NK Cells to Produce IFN-γ in Vivo and Increases the Toxicity of Lipopolysaccharides," *J. Immunol.* 156:4570-4575.

Damha, M.J. et al. (1993). "Oligoribonucleotide Synthesis: The Silyl-Phosphoramidite Method," Chapter 5 *In Protocols for Oligonucleotides and Analogs*. S. Agrawal, ed. Humana Press: Totowa, N.J. pp. 81-114.

Douglas et al. (1987). "Nanoparticles in Drug Delivery," *Crit. Rev. Ther. Drug. Carrier Syst.* 3:233-261.

Dumas et al. (1995). "Induction of Tolerance by Administration of Hapten-immunoglobulin Conjugates is Associated with Decreased Il-2 and IL-4 Production," *Arch. Dematol. Res.* 287:123-128.

Durali, D. et al. (May 1998). "Cross-Reactions Between the Cytotoxic T-Lymphocyte Responses of Human Immunodeficiency Virus-Infected African and European Patients," *Journal of Virology* 72(5):3547-3553.

Elkins et al. (1999). "Bacterial DNA Containing CpG Motifs Stimulates Lymphocyte-Dependent Protection of Mice Against Lethal Infection With Intracellular Bacteria," *J. Immunol.* 162:2291-2298.

Elsayed et al. (1991). "The Structual Requiements of Epitopes With IgE Binding Capacity Demonstrated by Three major Allergens From Fish, Egg and Tree Pollen," *Scand. J. Clin. Lab. Invest. Suppl.* 204:17-31.

Fearon et al. (Aug. 2003). "A Minimal Human Immunostimulatory CpG Motif that Potently Induces IFN-gamma and IFN-alpha Production," *European Journal of Immunology* 33(8):2114-2122.

Fornadley. (1998). "Allergy Immunotherapy," *Otolaryngol. Clin. North Am.* 31:111-127.

Fu et al. (1997). "Protective Cellular Immunity: Cytotoxic T-Lymphocyte Responses Against Dominant and Recessive Epitopes of Influenza Virus Nucleoprotein Induced by DNA Immunization," *J. Virol.* 71:2715-2721.

Gao et al. (1989). "Circularization of Oligonucleotides by Disulfide Bridge Formation," J. Immunol. 143:3007-3014.

Gao et al. (1995). "Identification and Characterization of T Helper Epitopes in the Nucleoprotein of Influenza A Virus," *Nucleic Acids Res.* 23:2025-2029.

Geneseq Database Accession No. V32079. "Sequence Alignment of SEQ ID No. 1 with WO 98/16247," created on Apr. 23, 1998.
Geneseq Database Accession No. V80102. "Sequence Alignment of SEQ ID No. 1 with WO 98/55495," created on Dec. 1998.
Geoghegan et al. (1992). "Site-Directed Conjugation of Nonpeptide Groups to Peptides and Proteins via Periodate Oxidation of a 2-Amino Alcohol. Application to Modification at N-Terminal Serine," *Bioconjug. Chem.* 3:138-146.
Goodchild. (1990). "Conjugates of Oligonucleotides and Modified Oligonucleotides: A Review of Their Synthesis and Properties," *Bioconjug. Chem.* 1:165.
Govorkova et al. (1997). "Cross-protection of mice immunized with different influenza A (H2) strains and challenged with viruses of the same HA subtype," *Acta Virol.* (1997) 41:251-257.
Grabarek et al. (1990). "Zero-Length Crosslinking Procedure with the Use of Active Esters," *Anal. Biochem.* 185:131-135.
Gramzinski et al. (1998). "Immune Response to a Hepatitis B DNA Vaccine in Aotus Monkeys: A Comparison of Vaccine Formulation, Route, and Method of Administration," *Mol. Med.* 4:109-118.
Granoff et al. (1993). "Effect of Immunity to the Carrier Protein on Antibody Responses to *Haemophilus influenzae* b conjugate vaccines," *Vaccine* 11:S46-51.
Granoff et al. (1997). "MF59 Adjuvant Enhances Antibody Responses of Infant Baboons immunized with *Haemophilus Influenzae* type b and *Neisseria meningitidis* group C Oligosaccharide-CRM197 Conjugate Vaccine," *Infection and Immunity* 65(5): 1710-1715.
Hackett et al. (1983). "Influenza Virus Site Recognized by a Murine Helper T Cell Specific for H1 Strains," *J. Exp. Med.* 158:294-302.
Hagiwara et al. (1987). "A New Drug Delivery System of Anticancer Agents: Activated Carbon Particles Adsorbing Anticancer Agents," In Vivo 1:241-252.
Hames et al. eds. (1984). *Transcription and Translation: A Practical Approach*, IRL Press: Oxford, Washington D.C. pp. vii-xiv (Table of Contents).
Haralambidis et al. (1990). "The Preparation of Polyamide-Oligonucleotide Probes Containing Multiple Non-radioactive Labels," *Nucleic Acids Res.* 18:501-505.
Haralambidis et al. (1990). "The Synthesis of Polyamide—Oligonucleotide Conjugate Molecules," *Nucleic Acids Res.* 18:493-499.
Horner et al. (1998). "Immunostimulatory DNA is a Potent Mucosal Adjuvant," *Cell Immunol.* 190:77-82.
Jäger et al. (1988). "Oligonucleotide N-Alkylphosphoramidates: Synthesis and Binding to Polynucleotides," *Biochem.* 27:7247-7246.
Jakob et al. (1998). "Activation of Cutaneous Dendritic Cells by CpG-Containing Oligodeoxynucleotides: A Role for Dendritic Cells in the Augmentation of Th1 Responses by Immunostimulatory DNA," *J. Immunol.* 161:3042-3049.
Kataoka et al. (1992). "Antitumor Activity of Synthetic Oligonucleotides with Sequences from cDNA Encoding Proteins of *Mycobacterium bovis* BCG," *Jpn. J. Cancer Res.* 83:244-247.
Kessler, C. (1992). "Nonradioactive labeling methods for nucleic acids" Chapter 2 *In Nonisotopic DNA Probe Techniques*, L.J. Kricka, ed. Academic Press, Inc.: San Diego, CA. pp. 29-92.
Kikuta, K. et al. (1990). "Cross-protection against influenza B type virus infection by intranasal inoculation of the HA vaccines combined with cholera toxin B subunit," *Vaccine* 8:595-599.
Kimura et al. (1994). "Binding of Oligoguanylate to Scavenger Receptors is Required for Oligonucleotides to Augment NK Cell Activity and Induce IFN," *J. Biochem.* (Tokyo) 116:991-994.
Kline et al. (1997). "Immune Redirection by CpG Oligonucleotides: Coversion of a Th2 Response to a Th1 Response in a Murine Model of Asthma," *J. Invest. Med.* 45(3):282A.
Klinman et al. (1996). "CpG Motifs Present in Bacterial DNA Rapidly Induce Lymphocytes to Secrete Interleukin 6, Interleukin 12, and Interferon Gamma," *Proc. Natl. Acad. Sci. USA.* 93:2879-2883.
Klinman et al. (1997). "Contribution of CpG Motifs to the Immunogenicity of DNA Vaccines," *J. Immunol.* 158:3635-3639.
Klinman, D.M. et al. (Jan. 1999). "CpG Motifs as Immune Adjuvants," *Vaccine* 17(1):19-25.

Kodihalli et al. (1997). "Cross-Protection Among Lethal H5N2 Influenza Viruses Induced by DNA Vaccine to the Hemagglutinin," *J. Virol.* 71:3391-3396.
Kovarik et al. (1999). "CpG Oligodeoxynucleotides can Circumvent the Th2 Polarization of Neonatal Responses to Vaccines but may Fail to Fully Redirect Th2 Responses Established by Neonatal Priming," *J. Immunol.* 162:1611-1617.
Kremsky et al. (1987). "Immobilization of DNA via Oligonucleotides Containing an Aldehyde or Carboxylic Acid Group at the 5' Terminus," *Nucleic Acids Res.* 15:2891-2909.
Krieg et al. (1989). "A Role for Endogenous Retroviral Sequences in the Regulation of Lymphocyte Activation," *J. Immunol.* 143:2448-2451.
Krieg et al. (1995). "CpG Motifs in Bacterial DNA Trigger Direct B-cell Activation," *Nature* 374:546-549.
Krieg et al. (1996). "Oligodeoxynucleotide Modifications Determine the Magintude of B Cell Stimulation by CpG Motifs," *Antisense Nucleic Acid Drug Dev.* 6:133-139.
Krieg et al. (1998a). "The Role of CpG Dinucleotides in DNA Vaccines," *Trends Microbiol.* 6:23-27.
Krieg et al. (1998b). "CpG DNA Induces Sustained IL-12 Expression in Vivo and Resistance to *Listeria monocytogenes* Challenge," *J. Immunol.* 161:2428-2434.
Krieg et al. (1998c). "Sequence Motifs in Adenoviral DNA Block Immune Activation by Stimulatory CpG Motifs," *Proc. Natl. Acad. Sci. USA* 95:12631-12636.
Krieg. (1996). "Lymphocyte Activiation by CpG Dinucleotide Motifs in Prokaryotic DNA," *Trends Microbiol.* 4(2):73-76.
Krieg. (1998). "Leukocyte Stimulation by Oligonucleotides," Chapter 24 *In Applied Antisense Oliqonucleotide Technology*. C.A. Stein et al. eds, Wiley-Liss, Inc. New York pp. 431-448.
Krieg. (1999). "CpG DNA: A Novel Immunomodulator," *Trends Microbiol.* 7:64-65.
Kullmann, W. ed. (1987). *Enzymatic Peptide Synthesis*, CRC Press, Inc.: Boca Raton, FL 3 pages total (Table of Contents).
Lambert et al. (1998). "Effect of Polyisobutylcyanoacrylate nanoparticles and Lipofectin® Loaded with Oligonucleotides on Cell Viability and a PKC Alpha Neosynthesis in HepG2 Cells," *Biochimie* 80:969-976.
Lasic, D.D. (1993). *Liposomes: From Physics to Applications*, Elsevier: New York, N.Y. pp. xi-xviii (Table of Contents).
Latimer et al. (1995). "Specificity of Monoclonal Antibodies Produced Against Phosphorothioate and Ribo Modified DNAs," *Mol. Immunol.* 32:1057-1064.
Lea et al. (1996). "Cloning and Sequencing of cDNA's Encoding the Human Sperm Protein Sp17," *Biochem. Biophys. Acta* 1307:263.
Leclerc et al. (1997). "The Preferential Induction of a Th1 Immune Response by DNA-Based Immunization is Mediated by the Immunostimulatory Effect of Plasmid DNA," *Cell. Immunol.* 179:97-106.
Lee, D.J. et al. (1998). "Control of Immune Responses by Gene Immunization,"*Ann Med.* 30(5):460-468.
Leff. (1997). "Muscle-Building Gene Sees Two-Track Payoff: Human Therapies, Animal Meat," *Bioworld* 86:1-2.
Lipford et al. (1997). "CpG-Containing Synthetic Oligonucleotides Promote B and Cytotoxic T Cell Responses to Protein Antigen: A New Class of Vaccine Adjuvants," *Eur. J. Immunol.* 27:2340-2344.
Lipford et al. (1997). "Immunostimulatory DNA: Sequence-dependent Production of Potentially Harmful or Useful Cytokines," *Eur. J. Immunol.* 27:3420-3426.
Liu et al. (1998). "Immunostimulatory CpG Oligodeoxynucleotides Enhance the Immune Response to Vaccine Strategies Involving Granulocyte-Macrophage Colony-Stimulating Factor," *Blood* 92:3730-3736.
MacFarlane et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step," *Immunology* 91:586-593.
Malley (1989). "The Immune Response of Offspring Mice from Mothers Immunized During Pregnancy with Protein Antigens," *J. Reprod. Immunol.* 16:173-186.

Martin-Orozco et al. (1999). "Enhancement of Antigen-Presenting Cell Surface Molecules Involved in Cognate Interactions by Immunostimulatory DNA Sequences," *Int. Immunol.* 11:1111-1118.

Matteucci. (1997). "Oligonucleotide Analogs: An Overview" In *Oligonucleotides as Therapeutic Agents*, D.J. Chadwick and G. Cardew, eds. John Wiley and Sons: New York, N.Y. pp. 5-18.

Mbawuike et al. (1994). "Influenza A Subtype Cross-Protection After Immunization of Outbred Mice with a Purified Chimeric NS1/HA2 Influenza Virus Protein," *Vaccine* 12:1340-1348.

McCluskie et al. (1998). "Cutting Edge: CpG DNA is a Potent Enhancer of Systemic and Mucosal Immune Responses Against Hepatitis B Surface Antigen with Intranasal Administration to Mice," *J. Immunol.* 161(9):4463-4466.

Merriam-Webster's Collegiate Dictionary, 10th edition (1993). Springfield, MA: Merriam-Webster, Incorporated, p. 235.

Miller et al. (1971). "Syntheses and Properties of Adenine and Thymidine Nucleoside Alkyl Phosphotriesters, the Neutral Analogs of Dinucleoside Monophosphates," *JACS* 93:6657-6665.

Mitragotri et al. (1995). "Ultrasound-Mediated Transdermal Protein Delivery," *Science* 269:850-853.

Mojcik et al. (1993). "Administration of a Phosphorothioate Oligonucleotide Antisense to Murine Endogenous Retroviral MCF env Causes Immune Effects in Vivo in a Sequence-Specific Manner," *Clin. Immuno. and Immunopathol.* 67:130-136.

Moldoveanu et al. (1998). "CpG DNA, a Novel Immune Enhancer for Systemic and Mucosal Immunization with Influenza Virus," *Vaccine* 16: 1216-1224.

Nelson et al. (1989). "Bifunctional Oligonucleotide Probes Synthesized using a Novel CPG Support are Able to Detect Single Base Pair Mutations," *Nucleic Acids Res.* 17:1781-1794.

Nelson et al. (1997). "N3'-P5' Oligodeoxyribonucleoside Phosphoramidates: A New Method of Synthesis Based on a Phosphoramidite Amine-Exchange Reaction," *JOC* 62:7278-7287.

O'Shannessy et al. (1985). "Specific Conjugation Reactions of the Oligosaccharide Moieties of Immunoglobulins," *J. Applied Biochem.* 7:347-355.

Pertmer et al. (1996). "Influenza Virus Nucleoprotein-Specific Immunoglobulin G Subclass and Cytokine Responses Elicited by DNA Vaccination are Dependent on the Route of Vector DNA Delivery," *J. Virol.* 70:6119-6125.

Peyrottes et al. (1996). "Oligodeoxynucleoside Phosphoramidates (P-NH2): Synthesis and Thermal Stability of Duplexes with DNA and RNA Targets," *Nucleic Acids Res.* 24:1841-1848.

Pisetsky (1996). "Immune Activation by Bacterial DNA: A New Genetic Code," *Immunity* 5:303-310.

Pisetsky (1996). "The Immunologic Properties of DNA," *J. Immunol.* 156:421-423.

Pisetsky et al. (1994). "Stimulation of Murine Lymphocyte Proliferation by a Phosphorothioate Oligonucleotide with Antisense Activity for Herpes Simplex Virus," *Life Sci.* 54(2):101-107.

Pisetsky et al. (1995). "Immunological Properties of Bacterial DNA," *Ann. N.Y. Acad. Sci.* 772:152-163.

Rafnar et al. (1991). "Cloning of Amb a I (Antigen E), the Major Allergen Family of Short Ragweed Pollen," *J. Biol. Chem.* 266:1229-1236.

Raz et al. (1994). "Intradermal Gene Immunization: The Possible Role of DNA Uptake in the Induction of Cellular Immunity to Viruses," *Proc. Natl. Acad. Sci. USA* 91:9519-9523.

Raz et al. (1996). "Preferential Induction of a TH1 Immune Response and Inhibition of Specific IgE Antibody Formation by Plasmid DNA Immunization," *Proc. Natl. Acad. Sci. USA* 93:5141-5145.

Redford et al. (1998). "Cyclosporin A Enhances IL-12 Production by CpG Motifs in Bacterial DNA and Synthetic Oligodeoxynucleotides," *J. Immunol.* 161:3930-3935.

Rogers et al. (1993). "Recombinant *Fel d* I: Expression, Purification, IgE Binding and Reaction with Cat-Allergic Human T Cells," *Mol. Immunol.* 30:559-568.

Roget et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17:7643-7651.

Roman et al. (1997). "Immunostimulatory DNA Sequences Function as T Helper-1-Promoting Adjuvants," *Nature Med.* 3:849-854.

Rose (1998). "A Proposal for a New Direction to Treat Cancer," *J. Ther. Biol.* 195:111-128.

Ruth, J.L. (1991). "Oligodeoxynucleotides with Reporter Groups Attached to the Base," Chapter 11 In *Oligonucleotides and Analogues: A Practical Approach*. F.Eckstein, ed. IRL Press: Oxford pp. 255-282.

Sato et al. (1996). "Immunostimulatory DNA Sequences Necessary for Effective Intradermal Gene Immunization," *Science* 273:352-354.

Scherle et al. (1986). "Differential Ability of B Cells Specific for External vs. Internal Influenza Virus Proteins to Respond to Help from Influenza Virus-Specific T-cell clones in vitro," *J. Exp. Med.* 164:1114-1128.

Scherle et al. (1988). "Functional Analysis of Influenza-Specific Helper T Cell Clones in Vivo," *Proc. Natl. Acad. Sci. USA* 85:4446-4450.

Schroeder et al. (1998). "Efficacy of Oral Dalargin-loaded Nanoparticle Delivery Across the Blood-Brain Barrier," *Peptides* 19:777-780.

Schultz et al. (1996). "Oligo-2'-fluoro-2'-deoxynucleotide N3'-P5' Phosphoramidates: Synthesis and Properties," *Nucleic Acids Res.* 24:2966-2973.

Schwartz et al. (1997). "CpG Motifs in Bacterial DNA Cause Inflammation in the Lower Respiratory Tract," *J. Clin. Invest.* 100:68-73.

Shimada et al. (1986). "In Vivo Augmentation of Natural Killer Cell Activity with a Deoxyribonucleic Acid Fraction of BCG," *Jpn. J. Cancer Res.* 77:808-816.

Shu et al. (1993). "Analysis of the Evolution and Variation of the Human Influenza A Virus Nucleoprotein Gene from 1933 to 1990," *J. Virol.* 67:2723-2729.

Sinha, N.D. et al. (1991). "Oligonucleotides with Reporter Groups Attached to the 5'-Terminus," Chapter 8 In *Oligonucleotide Analogues: A Practical Approach*. F. Eckstein, ed Irl Press: Oxford. pp. 185-210.

Sonehara et al. (1996). "Hexamer Palindromic Oligonucleotides with 5'-CG'3' Motif(s) Induce Production of Interferon," *J. Interferon and Cytokine Res.* 16:799-803.

Sparwasser et al. (1997). "Macrophages Sense Pathogens via DNA Motifs: Induction of Tumor Necrosis Factor-Alpha-Mediated Shock," *Eur. J. Immunol.* 27:1671-1679.

Spiegelberg et al. (1998). "Inhibition of IgE formation and Allergic Inflammation by Allergen Gene Immunization and by CpG Motif Immunostimulatory Oligodeoxynucleotides," *Allergy* 53(45S):93-97.

Spiegelberg et al. (1999). "Inhibition of Allergic Inflammation in the Lung by Plasmid DNA Allergen Immunization," *Pediatr. Pulmonol. Suppl.* 18:118-121.

Stacey et al. (1996). "Macrophages Ingest and Are Activated by Bacterial DNA," *J. Immunol.* 157:2116-2122.

Staros et al. (1986). "Enhancement by N-Hydroxysulfosuccinimide of Water-Soluble Carbodiimide-Mediated Coupling Reactions," *Anal. Biochem.* 156:220-222.

Stein, C.A. et al. (1997). "Non-Antisense Effects of Oligonucleotides," Chapter 11 In *Antisense Technology: A Practical Approach*. C. Lishtenstein et al., eds. IRL Press: Oxford. pp. 241-264.

Stirchak et al. (1989). "Uncharged Stereoregular Nucleic Acid Analogs: 2. Morpholino Nucleoside Oligomers with Carbamate Internucleoside Linkages," *Nucleic Acids Res.* 17:6129-6141.

Takahashi et al. (1990). "Induction of CD8+Cytotoxic T Cells by Immunization with Purified HIV-1 Envelope Protein in ISCOMs," *Nature* 344:873-875.

Tamura et al. (1992). "Superior Cross-Protective Effect of Nasal Vaccination to Subcutaneous Inoculation with Influenza Hemagglutinin Vaccine," *Eur. J. Immunol.* 22:477-481.

Tamura et al. (1994). "Formulation of Inactivated Influenza Vaccines for Providing Effective Cross-Protection by Intranasal Vaccination in Mice," *Vaccine* 12:310-316.

Tamura et al. (1998). "Definition of Amino Acid Residues on the Epitope Responsible for Recognition by Influenza A Virus H1-Specific, H2-Specific, and H1- and H2-Cross-Reactive Murine Cytotoxic T-Lymphocyte Clones," *J. Virol.* 72:9404-9406.

Tokunaga et al. (1992). "Synthetic Oligonucleotides with Particular Base Sequences from the cDNA Encoding Proteins of *Mycobacterium bovis* BCG Induce Interferons and Activate Natural Killer Cells," *Microbiol. Immunol.* 36:55-66.

Tokunaga et al. (1999). "How BCG Led to the Discovery of Immunostimulatory DNA," *Jpn. J. Infect. Dis.* 52:1-11.

Tung et al. (1991). "Preparation of Oligonucleotide-Peptide Conjugates," *Bioconjug. Chem.* 2:464-465.

Wang et al. (1994). "Circular RNA Oligonucleotides. Synthesis, Nucleic Acid Binding Properties, and a Comparison with Circular DNAs," *Nucleic Acids Res.* 22:2326-2333.

Warner et al. (1984). "Construction and Evaluation of an Instrument for the Automated Synthesis of Oligodeoxyribonucleosides," *DNA* 3:401.

Watwe et al. (1995). "Manufacture of Liposomes: A Review," *Curr. Sci.* 68:715-724.

Weeratna et al. (1998). "Reduction of Antigen Expression from DNA Vaccines by Coadministered Oligodeoxynucleotides," *Antisense & Nucleic Acid Drug Development* 8:351-356.

Weiner et al. (1997). "Immunostimulatory Oligodeoxynucleotides Containing the CpG Motif are Effective as Immune Adjuvants in Tumor Antigen Immunization," *Proc. Natl. Acad. Sci. USA* 94:10833-10837.

Wooldridge et al. (1997). "Immunostimulatory Oligodeoxynucleotides Containing CpG Motifs Enhance the Efficacy of Monoclonal Antibody Therapy of Lymphoma," *Blood* 89:2994-2998.

Yamamoto et al. (1992). "Unique Palindromic Sequences in Synthetic Oligonucleotides are Required to Induce INF and Augment INF-Mediated Natural Killer Activity," *J. Immunol.* 148:4072-4076.

Yamamoto et al. (1994). "Ability of Oligonucleotides with Certain Palindromes to Induce Interferon Production and Augment Natural Killer Cell Activity is Associated with their Base Length," Antisense Research and Development 4:119-122.

Yamamoto et al. (1994). "Synthetic Oligonucleotides with Certain Palindromes Stimulate Interferon Production of Human Peripheral Blood Lymphocytes in Vitro," *Jpn. J. Cancer Res.* 85:775-779.

Yanagawa et al. (1988). "Analysis of Superhelical Structures of Nucleic Acid-Lipid Conjugates by Image Processing," *Nucleic Acids Symp. Ser.* 19:189-192.

Yi et al. (1996). "IFN-Gamma Promotes IL-6 and IgM Secretion in Response to CpG Motifs in Bacterial DNA and Oligodeoxynucleotides," *J. Immunol.* 156:558-564.

Yi et al. (1998). "CpG DNA Rescue from Anti-IgM-Induced WEHI-231 B Lymphoma Apoptosis via Modulation of IkB Alpha and IkB Beta and Sustained Activation of Nuclear Factor-kB/c-Rel," *J. Immunol.* 160:1240-1245.

Yi et al. (1998). "CpG Motifs in Bacterial DNA Activate Leukocytes Through the pH-Dependent Generation of Reactive Oxygen Species," *J. Immunol.* 160:4755-4761.

Yi et al. (1998). "CpG Oligodeoxyribonucleotides Rescue Mature Spleen B Cells from Spontaneous Apoptosis and Promote Cell Cycle Entry," *J. Immunol.* 160:5898-5906.

Yi et al. (1998). "Cutting Edge: Rapid Induction of Mitogen-Activated Protein Kinases by Immune Stimulatory CpG DNA," J. Immunol. 161:4493-4497.

Zhao et al. (1996). "Effect of Different Chemically Modified Oligodeoxynucleotides on Immune Stimulation," *Biochem. Pharmacol.* 51:173-182.

Zimmermann et al. (1998). "Cutting Edge: CpG Oligodeoxynucleotides Trigger Protective and Curative Th1 Responses in Lethal Murine Leishmaniasis," *J. Immunol.* 160:3627-3630.

Zon, G. (1993). "Oligonucleoside Phosphorothioates," Chapter 8 In *Protocols for Oliognucleotides and Analogs, Synthesis and Properties*. Agrawal, ed. Humana Press:Totowa, N.J. pp. 165-189.

Zuckermann et al. (1987). "Efficient Methods for Attachment of Thiol Specific Probes to the 3'-Ends of Synthetic Oligodeoxyribonucleotides," *Nucleic Acids Res.* 15:5305-5321.

Davis, H.L. et al. (1998). "CpG DNA Is a Potent Enhancer of Specific Immunity in Mice Immunized with Recombinant Hepatitis B Surface Antigen," *Journal of Immunology* 160:870-876.

Kline, J.N. et al. (1998). "Cutting Edge: Modulation of Airway Inflammation by CpG Oligodeoxynucleotides in a Murine Model of Asthma," *Journal of Immunology* 160:2555-2558.

Klinman, D.M. (1998). "Therapeutic Applications of CpG-Containing Oligodeoxynucleotides," *Antisense and Nucleic Acid Drug Development* 8:181-184.

Krieg, A.M. (Aug. 1999). "Immune Stimulation by CpG DNA," *Antisense and Nucleic Acid Drug Development* 9(4):429-431.

Krieg, A.M. (1999). "Direct Immunologic Activities of CpG DNA and Implications for Gene Therapy," *The Journal of Gene Medicine* 1:56-63.

McCluskie, M.J. et al. (1999). "Novel Strategies Using DNA for the Induction of Mucosal Immunity," *Critical Reviews in Immunology* 19:303-329.

Scott, D. et al. (1984). "Immunogenicity of Biotinylated Hapten-Avidin Complexes," *Molecular Immunology* 21(11):1055-1060.

Stacey, K.J. et al. (Aug. 1999). "Immunostimulatory DNA as an Adjuvant in Vaccination Against *Leishmania major*," *Infection and Immunity* 67(8):3719-3726.

Vogel, F.R. et al. (1995). "A Compendium of Vaccine Adjuvants and Excipients ($2^{nd}$ Edition)," *Pharm. Biotechnol.* 6:141-228, pp. 1 and 34 only.

* cited by examiner

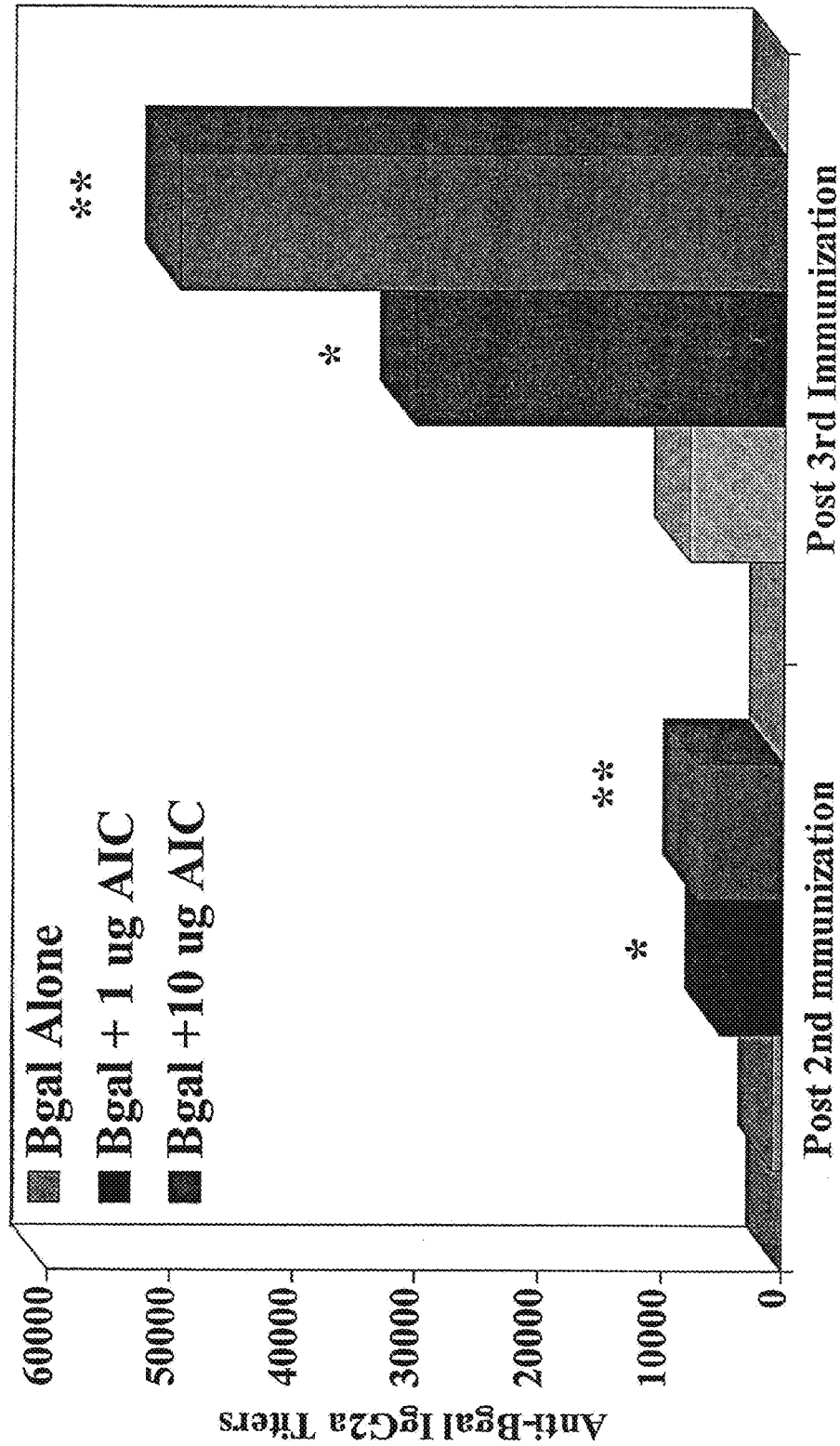

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
tgactgtgaa cgttcgagat ga                                            22

<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2
tgaccgtgaa cgttcgagat ga                                            22

<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3
tcatctcgaa cgttccacag tca                                           23

<210> SEQ ID NO 4
<211> LENGTH: 22
<212> TYPE: DNA
<213> ORGANISM: Artificial Sequence
<220> FEATURE:
<223> OTHER INFORMATION: Synthetic construct

<400> SEQUENCE: 4
tgactgtgaa cgttccagat ga                                            22

<210> SEQ ID NO 5
<211> LENGTH: 26
<212> TYPE: DNA
<213> ORGANISM: Artificial Sequence
```

-continued

<220> FEATURE:
<223> OTHER INFORMATION: Synthetic construct

<400> SEQUENCE: 5
tccataacgt tcgcctaacg ttcgtc 26

<210> SEQ ID NO 6
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (11)...(11)
<223> OTHER INFORMATION: N = 5-bromocytosine

<400> SEQUENCE: 6
tgactgtgaa ngttccagat ga 22

<210> SEQ ID NO 7
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (11)...(11)
<223> OTHER INFORMATION: N = 5-bromocytosine

<400> SEQUENCE: 7
tgactgtgaa ngttcgagat ga 22

<210> SEQ ID NO 8
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 11, 15
<223> OTHER INFORMATION: N = 5-bromocytosine

<400> SEQUENCE: 8
tgactgtgaa ngttngagat ga 22

<210> SEQ ID NO 9
<211> LENGTH: 24
<212> TYPE: PRT
<213> ORGANISM: Unknown
<220> FEATURE:
<223> OTHER INFORMATION: Synthetic construct using Influenza virus

<400> SEQUENCE: 9

Phe Trp Arg Gly Glu Asn Gly Arg Lys Thr Arg Ser Ala Tyr Glu Arg
1 5 10 15

Met Cys Asn Ile Leu Lys Gly Lys
20

<210> SEQ ID NO 10
<211> LENGTH: 9
<212> TYPE: PRT
<213> ORGANISM: Unknown
<220> FEATURE:
<223> OTHER INFORMATION: Synthetic construct using Influenza virus

```
<400> SEQUENCE: 10

Thr Tyr Gln Arg Thr Arg Ala Leu Val
1               5

<210> SEQ ID NO 11
<211> LENGTH: 9
<212> TYPE: PRT
<213> ORGANISM: Infleunza Virus
<220> FEATURE:
<223> OTHER INFORMATION: Synthetic construct using Influenza virus

<400> SEQUENCE: 11

Phe Glu Arg Phe Glu Ile Phe Pro Lys
1               5

<210> SEQ ID NO 12
<211> LENGTH: 9
<212> TYPE: PRT
<213> ORGANISM: Infleunza Virus
<220> FEATURE:
<223> OTHER INFORMATION: Synthetic construct using Influenza virus

<400> SEQUENCE: 12

Ile Tyr Ser Thr Val Ala Ser Ser Leu
1               5
```

METHODS OF MODULATING AN IMMUNE RESPONSE USING IMMUNOSTIMULATORY SEQUENCES AND COMPOSITIONS FOR USE THEREIN

CROSS-REFERENCE TO RELATED APPLICATIONS

This application is a continuation of U.S. patent application Ser. No. 09/642,492, filed Aug. 18, 2000, now U.S. Pat. No. 7,479,285, which claims the priority benefit of U.S. Provisional application 60/149,768, filed Aug. 19, 1999, each of which is hereby incorporated herein by reference in its entirety.

TECHNICAL FIELD

This invention relates to the field of immunology. More specifically, it pertains to methods of modulating an immune response to one antigen by administering another antigen in conjunction with an immunostimulatory polynucleotide.

BACKGROUND ART

Immunization, whereby antigen is administered in order to elicit an immune response, has been successful in preventing and treating a number of major disorders, including infectious diseases and, to a more limited extent, allergies. Immunization also holds promise in other areas, such as cancer. However, in several significant contexts, there have been limitations. In some instances, administration of antigen, even when using adjuvants, fails to elicit the desired immune response. Thus, the antigen itself cannot be rendered sufficiently immunogenic. In the case of some viruses, such as flu virus, the antigen changes often, typically from season to season, necessitating reformulation of the vaccines. In other instances, the type of immune response generated by immunizing with antigen is not the desired immune response. For example, most vaccines currently in use elicit effective humoral (antibody) responses, but fail to elicit cellular responses. This has been a major hurdle in the cancer context. Finally, often it is desirable to elicit protection against a number of antigens which would be encountered simultaneously, as in the case of allergens or certain infectious diseases, or even cancer. The ability to elicit more effectively an immune response against more than one antigen could prove to significantly enhance efficacy and expand the scope of immunization.

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

Other references describing ISS include: Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J. Cancer Res.* 85:775-779; Raz et al. (1994) *Proc. Natl. Acad. Sci. USA* 91:9519-9523; Kimura et al. (1994) *J. Biochem.* (Tokyo) 116:991-994; Krieg et al. (1995) *Nature* 374:546-549; Pisetsky et al. (1995) *Ann. N.Y. Acad. Sci.* 772:152-163; Pisetsky (1996a) *J. Immunol.* 156:421-423; Pisetsky (1996b) *Immunity* 5:303-310; Zhao et al. (1996) *Biochem. Pharmacol.* 51:173-182; Yi et al. (1996) *J. Immunol.* 156:558-564; Krieg (1996) *Trends Microbiol.* 4(2):73-76; Krieg et al. (1996) *Antisense Nucleic Acid Drug Dev.* 6:133-139; Klinman et al. (1996) *Proc. Natl. Acad. Sci. USA.* 93:2879-2883; Raz et al. (1996); Sato et al. (1996) *Science* 273:352-354; Stacey et al. (1996) *J. Immunol.* 157:2116-2122; Ballas et al. (1996) *J. Immunol.* 157:1840-1845; Branda et al. (1996) *J. Lab. Clin. Med.* 128:329-338; Sonehara et al. (1996) *J. Interferon and Cytokine Res.* 16:799-803; Klinman et al. (1997) *J. Immunol.* 158:3635-3639; Sparwasser et al. (1997) *Eur. J. Immunol.* 27:1671-1679; Roman et al. (1997); Carson et al. (1997) *J. Exp. Med.* 186:1621-1622; Chace et al. (1997) *Clin. Immunol. and Immunopathol.* 84:185-193; Chu et al. (1991) *J. Exp. Med.* 186:1623-1631; Lipford et al. (1997a) *Eur. J. Immunol.* 27:2340-2344; Lipford et al. (1997b) *Eur. J. Immunol.* 27:3420-3426; Weiner et al. (1997) *Proc. Natl. Acad. Sci. USA* 94:10833-10837; Macfarlane et al. (1997) *Immunology* 91:586-593; Schwartz et al. (1997) *J. Clin. Invest.* 100:68-73; Stein et al. (1997) *Antisense Technology*, Ch. 11 pp. 241-264, C. Lichtenstein and W. Nellen, Eds., IRL Press; Wooldridge et al. (1997) *Blood* 89:2994-2998; Leclerc et al. (1997) *Cell. Immunol.* 179:97-106; Kline et al. (1997) *J. Invest. Med.* 45(3):282A; Yi et al. (1998a) *J. Immunol.* 160:1240-1245; Yi et al. (1998b) *J. Immunol.* 160:4755-4761; Yi et al. (1998c) *J. Immunol.* 160:5898-5906; Yi et al. (1998d) *J. Immunol.* 161:4493-4497; Krieg (1998) *Applied Antisense Oligonucleotide Technology* Ch. 24, pp. 431-448, C. A. Stein and A. M. Krieg, Eds., Wiley-Liss, Inc.; Krieg et al. (1998a) *Trends Microbiol.* 6:23-27; Krieg et al. (1998b) *J. Immunol.* 161:2428-2434; Krieg et al. (1998c) *Proc. Natl. Acad. Sci. USA* 95:12631-12636; Spiegelberg et al. (1998) *Allergy* 53(45S):93-97; Horner et al. (1998) *Cell Immunol.* 190:77-82; Jakob et al. (1998) *J. Immunol.* 161:3042-3049; Redford et al. (1998) *J. Immunol.* 161:3930-3935; Weeratna et al. (1998) *Antisense & Nucleic Acid Drug Development* 8:351-356; McCluskie et al. (1998) *J. Immunol.* 161(9):4463-4466; Gramzinski et al. (1998) *Mol. Med.* 4:109-118; Liu et al. (1998) *Blood* 92:3730-3736; Moldoveanu et al. (1998) *Vaccine* 16: 1216-1224; Brazolot Milan et al. (1998) *Proc. Natl. Acad. Sci. USA* 95:15553-15558; Briode et al. (1998) *J. Immunol.* 161:7054-7062; Briode et al. (1999) *Int. Arch. Allergy Immunol.* 118:453-456; Kovarik et al. (1999) *J. Immunol.* 162:1611-1617; Spiegelberg et al. (1999) *Pediatr. Pulmonol. Suppl.* 18:118-121; Martin-Orozco et al. (1999) *Int. Immunol.* 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) *J. Immunol.* 162:2291-2298; WO 98/52962; WO 99/33488; WO 99/33868; WO 99/51259 and WO 99/62923. See also Zimmermann et al. (1998) *J. Immunol.* 160:3627-3630; Krieg (1999) *Trends Microbiol.* 7:64-65 and U.S. Pat. Nos. 5,663,153, 5,723,335 and 5,849,719.

As pathogens and allergy-inducing sources generally contain more than one immunogen or allergen, respectively, it would be especially desirable to enhance and/or modulate an immune response to the multiple antigens that are encountered upon, for example, viral infection or exposure to an allergy-inducing source. The present invention provides methods that can be employed in these contexts.

All publications and references cited herein are hereby incorporated by reference in their entirety.

DISCLOSURE OF THE INVENTION

The present invention provides methods which achieve modulation of an immune response against a second antigen, which is mediated by administration of a first antigen in conjunction with an immunostimulatory polynucleotide sequence.

Accordingly, in one aspect, the invention provides methods of modulating an immune response to a second antigen in an individual, comprising administering to the individual (preferably a mammal, more preferably a human) an immunomodulatory polynucleotide comprising an immunostimulatory sequence (ISS) and a first antigen, wherein the ISS-containing immunomodulatory polynucleotide and first antigen are administered in an amount sufficient to modulate an immune response to the second antigen upon exposure to the second antigen. In embodiments in which second antigen is not administered (i.e., first antigen is administered in absence of administration of second antigen), exposure to the second antigen is concurrent with first antigen. Preferably, the modulation of the immune response is stimulation of a Th1 response to the second antigen.

The first antigen and ISS containing polynucleotide may be co-administered in a variety of forms, including spatially proximate to one another (i.e., a generally fixed spatial relationship) or in an admixture. An antigen and ISS-containing polynucleotide may be proximately associated by conjugation, encapsulation, adsorption onto a surface, or linkage to a platform molecule. The first antigen can be any of a number of molecules, including moieties derived from infectious agents, such as virus or bacteria, allergens and carrier molecules. The first antigen may be associated with a carrier molecule.

In some aspects, the first antigen and ISS-containing polynucleotide are proximately associated, and are administered with a second antigen (i.e., one or more additional antigens). The second antigen may be any of a number of moieties, as described herein. Such administration results in modulation of an immune response to the second antigen(s), preferably a Th1 response.

The first antigen and ISS-containing polynucleotide (with or without second antigen) may be administered at any of a variety of times before and/or during exposure to the second antigen. In some embodiments, the ISS-containing polynucleotide and first antigen are administered upon exposure to the second antigen. The second antigen may or may not be encountered at the same site as the site of administration of the first antigen and ISS-containing polypeptide.

ISS are described herein, and generally comprise the sequence 5'-cytosine, guanine-3', more particularly comprise the sequence 5'-purine, purine, C, G, pyrimidine, pyrimidine-3' (such as 5'-AACGTT-3'). In some embodiments, the ISS generally comprises the sequence 5'-T,C,G-3'.

The invention also provides immunogenic compositions comprising a carrier molecule and an immunomodulatory polynucleotide comprising an ISS, preferably further comprising a pharmaceutically acceptable excipient. These compositions may further include an antigen (other than the carrier molecule). The invention also provides immunogenic compositions comprising an ISS-containing polynucleotide proximately associated with a first antigen and further comprising one or more additional antigens.

BRIEF DESCRIPTION OF THE DRAWINGS

FIG. 1 is a bar graph depicting the effect of administration of an ISS-Amb a 1 conjugate ("AIC") on β-gal IgG2a response (which indicates a Th1 response) in mice. Left hand bar, administration of β-gal alone; middle bar, administration of β-gal with 1 μg conjugate; right hand bar, administration of β-gal and 10 μg conjugate.

MODES FOR CARRYING OUT THE INVENTION

We have discovered that administration of a first antigen with an immunomodulatory polynucleotide comprising an immunostimulatory sequence(s) (ISS) elicits an immune response, particularly a Th1 response, to a second antigen. Modulating the immune response to an additional antigen in response to administration of a first antigen offers distinct benefits and advantages. This immunotherapeutic approach obviates or at least reduces the need for having to design and manufacture various formulations reflecting different antigenic compositions. It also mitigates the requirement for identification of all relevant antigens for immunotherapy. For example, allergy desensitization therapy could be accomplished by administration of an ISS-containing polynucleotide and just one antigen. This is especially significant in some contexts, such as with cockroach, which contains many antigens. This may also be beneficial for relief from different allergens which, due to seasonal and geographical parameters, are encountered together. Further, with respect to immunization against pathogens (whether prophylactic or therapeutic) rapid mutations in antigenic proteins, such as coat proteins, would not necessitate identification of the changes and concomitant reformulation of vaccines to reflect the mutations. In the context of antigens administered in the form of antigen-carrier conjugates, such as oligosaccharide antigens, administration of one such conjugate with an ISS-containing polynucleotide would modulate the immune response to another antigen when administered with the same protein carrier. The immune response to the second antigen could be obtained without the need to generate additional formulations.

We have further discovered that one or more benefits associated with administration of an ISS-containing polynucleotide spatially proximate to a first antigen, namely immune modulation at a significantly lower dose, stronger interferon γ response and an enhanced CTL response, are also observed with respect to a second antigen upon administration of a second antigen (i.e., one or more additional antigens) with an ISS-containing polynucleotide spatially proximate to a first antigen. This finding has significant, positive implications in terms of dosing (in that lower dosages may be required to obtain the desired response) as well as practical, manufacturing considerations (in that there is a reduced need to link additional antigens to an ISS-containing polynucleotide in order to obtain the benefit of such linkage).

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); and *Methods of Immunological Analysis* (R. Masseyeff, W. H. Albert, and N. A. Staines, eds., Weinheim: VCH Verlags gesellschaft mbH, 1993).

DEFINITIONS

As used herein, the singular form "a", "an", and "the" includes plural references unless indicated otherwise. For example, "a" second antigen includes one or more additional antigens.

The term "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4$^+$ T lymphocytes, CD8$^+$ T lymphocytes, B lymphocytes, and the like. Preferably, the ISS sequences preferentially activate a Th1-type response. A polynucleotide for use in methods of the invention contains at least one ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments.

The term "immunomodulatory" or "modulating an immune response" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, CD4$^+$ T lymphocytes, CD8$^+$ T lymphocytes, macrophages and the like; increased synthesis of immunostimulatory cytokines including, but not limited to, IL-1, IL-2, IL-4, IL-5, IL-6, IL-10, IL-12, IFN-α, IFN-β, IFN-γ, TNF-α and the like. Immunosuppressive effects include those that directly or indirectly decrease cellular or humoral immune responses. Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-γ, which appears to block IL-4 induced class switch to IgE and IgG1, thereby reducing the levels of these antibody subclasses.

The term "conjugate" refers to a complex in which an ISS-containing polynucleotide and an antigen are linked. Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, gangliosides and lipids; portions thereof and combinations thereof. The antigens can be those found in nature or can be synthetic. Haptens are included within the scope of "antigen." A hapten is a low molecular weight compound that is not immunogenic by itself but is rendered immunogenic when conjugated with an immunogenic molecule containing antigenic determinants.

A "second antigen" refers to an antigen other than a first antigen (including a different antigenic region within the same polypepeptide) which is encountered (i.e., by an environmental exposure) by and/or administered to an individual, and against which an immune response is modulated by the methods of the invention. As described herein, in some embodiments, a second antigen is administered in addition to an ISS-containing polynucleotide proximately associated with a first antigen.

A "carrier molecule" refers to an immunogenic molecule used in association with an antigen, usually by covalent linkage, to facilitate, cause and/or modulate an immune response to the antigen. Examples of carriers are provided herein.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g. antibody production or cytokine activity whether or not the peptide is a hapten. Typically, the peptides are of at least six amino acid residues in length. The term "peptide" further includes modified amino acids, such modifications including, but not limited to, phosphorylation, glycosylation, pegylation, lipidization and methylation.

A "conserved" or "constant" polypeptide is a term understood by those in the art and generally refers to a polypeptide (or a region or domain of a polypeptide) that does not mutate, or change its sequence, at an appreciable rate. A polypeptide, even a polypeptide that has variable regions, may comprise one or more conserved regions, or domains, and the terms "conserved" or "constant" or "preserved" polypeptides encompasses polypeptides consisting of, as well as comprising, these conserved regions. Thus a "conserved" or "constant" polypeptide may be a complete or partial sequence. The term "constant domain" includes regions of antigens that are not prone to vary between strains and/or species of virus. Generally, an amino acid sequence comparison indicates conserved polypeptides (including conserved regions of polypeptides), although three-dimensional conformation may be conserved although sequences appear to be different. For purposes of this invention, "conserved" usually pertains to sequence conservation. As understood in the art, a "constant" polypeptide is distinguished from a "variable" polypeptide (which includes variable regions or domains), which refers to a polypeptide that does mutate at an appreciable rate. Thus the terms "constant" and "variable" are relative. Examples of a variable peptides are some viral coat proteins. Coat proteins include, but are not limited to, HIV envelope proteins, influenza virus hemagglutinin (HA) protein and influenza virus neuraminidase (NA) protein. As this definition makes clear, a conserved viral core protein may be the entire core sequence or a portion of that sequence.

The term "immunomodulatory facilitator" refers to molecules which support and/or enhance the immunomodulatory activity of an ISS. Examples of immunomodulatory facilitators include co-stimulatory molecules, such as cytokines, and/or adjuvants.

A "delivery molecule" or "delivery vehicle" is a chemical moiety which facilitates, permits, and/or enhances delivery of an ISS and/or antigen to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheat and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:1111-127.

An "individual" is a vertebrate, preferably a mammal, more preferably a human. Mammals include, but are not limited to, humans, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to a second antigen, an effective amount of a composition comprising an ISS and a first antigen is an amount sufficient to achieve such a modulation as compared to the immune response obtained when the second antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

A second antigen which is encountered by an individual "concurrently" with a first antigen generally means at approximately the same time, and does not necessarily mean (although the term does encompass) exactly the same time. For example, a second antigen may be encountered within a number of hours, days, or weeks of encountering the first antigen. The second antigen may or may not be encountered at the same site (or location) that the first antigen is encountered. Thus, the second antigen may be encountered at the same site that the first antigen is encountered within a number of hours, days, or weeks of encountering the first antigen. Alternatively, the second antigen may be encountered at a different site than the site that the first antigen is encountered within a number of hours, days, or weeks of encountering the first antigen.

An ISS-containing polynucleotide and an antigen that are "proximately associated", in "proximate association" or "spatially proximate" refers to an arrangement which maintains the ISS-containing polynucleotide and antigen at an average distance. Generally, and most preferably, this distance is effective to enhance an immune response generated compared to the administration of the ISS-containing polynucleotide and antigen as an admixture. As described herein, there are various ways to effect "proximate association", such as conjugation, encapsulation, adsorption, and via a platform molecule.

METHODS OF THE INVENTION

The invention provides methods of modulating an immune response to a second antigen in an individual, preferably a mammal, more preferably a human, comprising administering to the individual an immunomodulatory polynucleotide comprising an ISS and a first antigen. For purposes of this invention, the immunomodulatory (i.e., ISS-containing) polynucleotide and first antigen are administered in an amount sufficient to modulate an immune response to a second antigen upon exposure to that antigen.

For purposes of this invention, antigens are introduced to an individual in either or both of two phases: administration, in which a first antigen and ISS-containing polynucleotide (with or without a second antigen) are deliberately introduced; and encounter, when one or more antigens are introduced to the individual via some form of environmental exposure. For purposes of this invention, an individual may or may not have been previously exposed to the first or second antigen before administration of the ISS-containing polynucleotide and first antigen (i.e., the individual may or may not be naïve with respect to the first and/or second antigens).

In some embodiments, a second antigen is not administered with the first antigen and ISS-containing polynucleotide. In these embodiments, the second antigen is encountered by the individual in the presence of (i.e., concomitantly or concurrently with) the first antigen. That is, for the methods of this invention to be effective, after administration of the ISS-containing polynucleotide and first antigen, the individual should concurrently encounter the first and second antigen in order to elicit the desired immune response to second antigen.

In other embodiments, a second antigen is administered with an ISS-containing polynucleotide which is proximately associated with a first antigen. In these embodiments, the second antigen need not be encountered by the individual in the presence of (i.e., concomitantly or concurrently with) the first antigen (i.e., the second antigen(s) may be encountered alone). Methods to accomplish proximate association of antigen and ISS-containing polynucleotide are discussed below.

Descriptions of ISS and first antigens which may be used in the present invention are provided below. The ISS and the first antigen can be co-administered in an admixture sufficiently close in time so as to modulate an immune response to the antigen (i.e., co-administered). Preferably, the ISS and the first antigen are administered simultaneously. In some embodiments, the polynucleotide comprising an ISS is linked to, or proximately associated to, a first antigen. Also described below are various ways of proximately associating the immunomodulatory polynucleotide with first antigen.

It is understood that an immune response may be elicited against one or more additional antigens. Thus, the invention encompasses methods by which an immune response is elicited against a third, fourth, fifth, etc., antigen. Preferably, the immune response is modulated by stimulation of a Th1 response. In other embodiments, the immune response is modulated by suppression of the Th2 response. An immune response may be a primary response and/or a memory T cell response.

In some embodiments, administration of the first antigen and ISS-containing polynucleotide occurs at the same site as the second antigen is and/or will be encountered. For example, if the second antigen is encountered at the mucosa, such as lung or vaginal tissue, then the immunomodulatory polynucleotide and first antigen are administered to the relevant mucosa. In other embodiments, the immunomodulatory polynucleotide and first antigen are administered at a site other than where the second antigen is encountered. For example, in the case of certain allergens, the immunomodulatory polynucleotide-first antigen is administered by injection, while the second antigen is encountered through the nasal passages.

ISS

In accordance with the present invention, the immunomodulatory polynucleotide contains at least one ISS, and can contain multiple ISSs. The ISSs can be adjacent within the polynucleotide, or they can be separated by additional nucleotide bases within the polynucleotide.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995); Yamamoto et al. (1992); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156:4570-4575; Roman et al. (1997); and Lipford et al. (1997a).

The ISS can be of any length greater than 6 bases or base pairs and generally comprises the sequence 5'-cytosine, guanine-3', more particularly comprises the sequence 5'-purine, purine, C, G, pyrimidine, pyrimidine-3' (such as 5'-AACGTT-3'), preferably greater than 15 bases or base pairs, more preferably greater than 20 bases or base pairs in length. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As is evident from the following embodiments, an ISS may also comprise 5'-T,C,G-3'.

In some embodiments, the ISS comprises any of the following sequences: GACGCTCC; GACGTCCC; GACGTTCC; GACGCCCC; AGCGTTCC; AGCGCTCC; AGCGTCCC; AGCGCCCC; AACGTCCC; AACGCCCC; AACGTTCC; AACGCTCC; GGCGTTCC; GGCGCTCC; GGCGTCCC; GGCGCCCC; GACGCTCG; GACGTCCG; GACGCCCG; GACGTTCG; AGCGCTCG; AGCGTTCG; AGCGTCCG; AGCGCCCG; AACGTCCG; AACGCCCG;

AACGTTCG; AACGCTCG; GGCGTTCG; GGCGCTCG; GGCGTCCG; GGCGCCCG. In some embodiments, the immunomodulatory polynucleotide comprises the sequence 5'-TGACTGTGAACGTTCGAGATGA-3' (SEQ ID NO:1). In other embodiments, the ISS comprises any of the sequences: 5'-TGACCGTGAACGTTCGAGATGA-3' (SEQ ID NO:2); 5'-TCATCTCGAACGTTCCACAGTCA-3' (SEQ ID NO:3); 5'-TGACTGTGAACGTTCCAGATGA-3' (SEQ ID NO:4); 5'-TCCATAACGTTCGCCTAACGTTCGTC-3' (SEQ ID NO:5); 5'-TGACTGTGAABGTTCCAGATGA-3' (SEQ ID NO:6), where B is 5-bromocytosine; 5'-TGACTGT-GAABGTTCGAGATGA-3' (SEQ ID NO:7), where B is 5-bromocytosine and 5'-TGACTGTGAABGTTB-GAGATGA-3' (SEQ ID NO:8), where B is 5-bromocytosine.

An ISS and/or ISS-containing polynucleotide may contain modifications. Modifications of ISS include any known in the art, but are not limited to, modifications of the 3'OH or 5'OH group, modifications of the nucleotide base, modifications of the sugar component, and modifications of the phosphate group. Various such modifications are described below.

An ISS may be single stranded or double stranded DNA, as well as single or double-stranded RNA or other modified polynucleotides. An ISS may or may not include one or more palindromic regions, which may be present in the hexameric motif described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in in *Protocols for Oligonucleotides and Analogs, Synthesis and Properties* (Agrawal, ed.) Humana Press, Totowa, N.J.; Warner et al. (1984) *DNA* 3:401 and U.S. Pat. No. 4,458,066.

The ISS can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in *Oligonucleotides as Therapeutic Agents*, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in *Protocols for Oligonucleotides and Analogs, Synthesis and Properties* (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Oligonucleotides with phosphorothioate backbones can be more immunogenic than those with phosphodiester backbones and appear to be more resistant to degradation after injection into the host. Braun et al. (1988) *J. Immunol.* 141: 2084-2089; and Latimer et al. (1995) *Mol. Immunol.* 32:1057-1064.

An ISS can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-O-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS may comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

In some embodiments, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an ISS-containing polynucleotide is greater than about any of the following lengths (in bases or base pairs): 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000.

First Antigen

The invention applies to any antigen, and, for embodiments in which a second antigen is not co-administered with the first antigen and ISS-containing polynucleotide, is particularly suited to those contexts in which an individual will be exposed to first and second antigens at approximately the same time. The second antigen may or may not be identified, and the first and second antigen may or may not be related, in terms of source. For example, there are a significant number of different grasses, trees and weeds (including ragweed, in which Amb a 1 is immunodominant and has been the most well-characterized), which cause allergy problems during certain seasons. Using the methods and/or compositions of the invention, Amb a 1 could be administered with the ISS, and an immune response, particularly a Th1 immune response, would be mounted against other antigens which would be expected to be encountered concurrently during ragweed season. As another example, individuals often have multiple allergies. In this instance, an ISS is administered with any allergen (with respect to the individual) and the individual mounts a Th1 response to other allergen(s). As another example, viruses typically are comprised of proteins which tend to be conserved, and thus relatively constant in sequence (i.e., do not mutate at a frequent rate) and proteins which are variable. In this context, the first antigen may be a constant polypeptide (such as a core polypeptide or a group- or sub-group specific, internal antigen), which, when administered with an ISS, would modulate an immune response against the virus' variable polypeptides (such as outer coat or type-specific antigens).

In some embodiments, the first antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229-1236), major dust mite allergens Der pI and Der PII (Chua et al. (1988) *J. Exp. Med.* 167:175-182; Chua et al. (1990) *Int. Arch. Allergy Appl. Immunol.* 91:124-129), white birch pollen Bet vI (Breiteneder et al. (1989) *EMBO J.* 8:1935-1938), domestic cat allergen Fel d I (Rogers et al. (1993) *Mol. Immunol.* 30:559-568), and protein antigens from tree pollen (Elsayed et al. (1991) *Scand. J. Clin. Lab. Invest. Suppl.* 204:17-31). Preparation of protein antigens from grass pollen for in vivo administration has been reported. Malley (1989) *J. Reprod. Immunol.* 16:173-186. Table 1 shows a list of allergens that may be used.

TABLE 1

RECOMBINANT ALLERGENS

| Group | Allergen | Reference |
|---|---|---|
| ANIMALS: CRUSTACEA | | |
| Shrimp/lobster | tropomyosin | Leung et al. J Allergy Clin Immunol, 1996, 98: 954-61 |
| | Pan s I | Leung et al. Mol Mar Biol Biotechnol, 1998, 7: 12-20 |

TABLE 1-continued

| RECOMBINANT ALLERGENS | | |
|---|---|---|
| Group | Allergen | Reference |
| INSECTS | | |
| Ant | Sol i 2 (venom) | Schmidt et al. J Allergy Clin Immunol., 1996, 98: 82-8 |
| Bee | phospholipase A2 (PLA) | Muller et al. J Allergy Clin Immunol, 1995, 96: 395-402 |
| | | Forster et al. J Allergy Clin Immunol, 1995, 95: 1229-35 |
| | | Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-80 |
| | Bla g 4 (a calycin) | Vailes et al. J Allergy Clin Immunol, 1998, 101: 274-80 |
| | glutathione S-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4 |
| | | Hakkaart et al. Clin Exp Allergy, 1998, 28: 169-74 |
| | | Hakkaart et al. Clin Exp Allergy, 1998, 28: 45-52 |
| | | Hakkaart et al. Int Arch Allergy Immunol, 1998, 115 (2): 150-6 |
| | | Mueller et al. J Biol Chem, 1997, 272: 26893-8 |
| | Der p 2 variant | Smith et al. J Allergy Clin Immunol, 1998, 101: 423-5 |
| | Der f 2 | Yasue et al. Clin Exp Immunol, 1998, 113: 1-9 |
| | | Yasue et al. Cell Immunol, 1997, 181: 30-7 |
| | Der p 10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase, and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
| | | Hoffmann et al. J Allergy Clin Immunol, 1997, 99: 227-32 |
| | | Hedlin Curr Opin Pediatr, 1995, 7: 676-82 |
| Cow | Bos d 2 (dander; a lipocalin) | Zeiler et al. J Allergy Clin Immunol, 1997, 100: 721-7 |
| | | Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 |
| | | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
| | | Spitzauer et al. J Allergy Clin Immunol, 1994, 93: 614-27 |
| | | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 |
| | | Grammer et al. J Lab Clin Med, 1987, 109: 141-6 |
| | | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 | Twardosz et al. Biochem Bioph. Res Comm., 1997, 239: 197 |
| | rBet v 1 Bet v 2: (profilin) | Pauli et al. J Allergy Clin Immunol, 1996, 97: 1100-9 |
| | | van Neerven et al. Clin Exp Allergy, 1998, 28: 423-33 |
| | | Jahn-Schmid et al. Immunotechnology, 1996, 2: 103-13 |
| | | Breitwieser et al. Biotechniques, 1996, 21: 918-25 |
| | | Fuchs et al. J Allergy Clin Immunol, 1997, 100: 356-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
| | | Lehrer et al. Int Arch Allergy Immunol, 1997, 113: 122-4 |

TABLE 1-continued

RECOMBINANT ALLERGENS

| Group | Allergen | Reference |
|---|---|---|
| Grass | Phl p 1, Phl p 2, Phl p 5 (timothy grass pollen) | Bufe et al. Am J Respir Crit Care Med, 1998, 157: 1269-76<br>Vrtala et al. J Immunol Jun. 15, 1998, 160: 6137-44<br>Niederberger et al. J Allergy Clin Immun., 1998, 101: 258-64 |
| | Hol 1 5 velvet grass pollen | Schramm et al. Eur J Biochem, 1998, 252: 200-6 |
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |
| | Cyn d 12 (a profilin) | Asturias et al. Clin Exp Allergy, 1997, 27: 1307-13<br>Fuchs et al. J Allergy Clin Immunol, 1997, 100: 356-64 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9<br>Fuchs et al. J Allergy Clin Immunol, 1997, 100: 356-64 |
| Mercurialis | Mer a I (profilin) | Vallverdu et al. J Allergy Clin Immunol, 1998, 101: 363-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6<br>Burks et al. J Clin Invest, 1995, 96: 1715-21<br>Burks et al. Int Arch Allergy Immunol, 1995, 107: 248-50 |
| *Poa pratensis* | Poa p9 | Parronchi et al. Eur J Immunol, 1996, 26: 697-703<br>Astwood et al. Adv Exp Med Biol, 1996, 409: 269-77 |
| Ragweed | Amb a I | Sun et al. Biotechnology August 1995, 13: 779-86<br>Hirschwehr et al. J Allergy Clin lmmunol, 1998, 101: 196-206<br>Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64<br>Donovan et al. Electrophoresis, 1993, 14: 917-22 |
| FUNGI: | | |
| *Aspergillus* | Asp f 1, Asp f 2, Asp f3, Asp f 4, rAsp f 6 | Crameri et al. Mycoses, 1998, 41 Suppl 1: 56-60<br>Hemmann et al. Eur J Immunol, 1998, 28: 1155-60<br>Banerjee et al. J Allergy Clin Immunol, 1997, 99: 821-7<br>Crameri Int Arch Allergy Immunol, 1998, 115: 99-114<br>Crameri et al. Adv Exp Med Biol, 1996, 409: 111-6<br>Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| Blomia | allergen | Caraballo et al. Adv Exp Med Biol, 1996, 409: 81-3 |
| *Penicillinium* | allergen | Shen et al. Clin Exp Allergy, 1997, 27: 682-90 |
| Psilocybe | Psi c 2 | Horner et al. Int Arch Allergy Immunol, 1995, 107: 298-300 |

In some embodiments, the first antigen is a viral conserved, or constant polypeptide, such as a core polypeptide. Administration of an ISS with an antigen comprising a constant polypeptide (which includes constant domain(s), region(s), or fragment(s) of a constant polypeptide) results in a Th1-type response to the viral antigen with the constant domain. Upon viral infection and exposure to all the viral antigens, an immune response to the constant domain antigen as well as to other antigens, including those which vary between strains, is mounted.

Conserved polypeptides include, but are not limited to, core proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J. Immunol.* 22:477-481; Hirabayashi et al. (1990) *Vaccine* 8:595-599. Other examples of conserved polypeptides are group- or sub-group specific antigens, which are known for a number of infectious agents, including, but not limited to, adenovirus, herpes simplex virus, papilloma virus, respiratory syncytial virus and poxviruses.

In some embodiments, the first antigen is linked to or associated with a carrier molecule. Typically, such an antigen is conjugated to the carrier molecule. In other embodiments, first antigen is a carrier molecule. In embodiments comprising a carrier molecule, the ISS containing polynucleotide may or may not be proximately associated (such as by conjugation) to the carrier molecule. In some embodiments, both the first antigen and the ISS are conjugated to the carrier molecule.

Carriers are known in the art. Plotkin, *Vaccines* 3rd Ed. Philadelphia, WB Saunders Co. (1999). Bacterial carriers (i.e., carriers derived from bacteria) include, but are not limited to, cholera toxin B subunit (CTB); diphtheria toxin mutant (CRM197); diphtheria toxoid; group B streptococcus alpha C protein; meningococcal outer membrane protein (OMPC); tetanus toxoid; outer membrane protein of nontypeable *Haemophilus influenza* (such as P6); recombinant class 3 porin (rPorB) of group B meningococci; heat-killed *Brucella abortus*; heat-killed *Listeria monocytogenes*; and *Pseudomonas aeruginosa* recombinant exoprotein A. Another carrier is keyhole limpet hemocyanin (KLH). Examples of viral-derived carriers are known in the art and include hepatitis b surface antigen (HBsAg) particles and hepatitis b core antigen (HBcAg). In some embodiments, the first antigen comprises a viral vector, such as vaccinia, adenovirus, and canary pox.

Many antigenic peptides and proteins are known, and available in the art; others can be identified using conventional techniques. For immunization against tumor formation, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the first antigen is an antigen from an infectious agent, including protozoan, bacterial, fungal (including unicellular and multicellular), and viral infectious agents. Examples of suitable viral antigens have been described above. Bacteria include *Hemophilus influenza*, *Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362: 833-839. Proteolytic enzymes can also be utilized to couple amino acids to produce peptides. Kullmann (1987) *Enzymatic Peptide Synthesis*, CRC Press, Inc. Alternatively, the peptide can be obtained by using the biochemical machinery of a cell, or by isolation from a biological source. Recombinant DNA techniques can be employed for the production of peptides. Hames et al. (1987) *Transcription and Translation: A Practical Approach*, IRL Press. Peptides can also be isolated using standard techniques such as affinity chromatography.

Preferably the antigens are peptides, lipids (e.g. sterols, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Second Antigen

In some embodiments, a second antigen is administered with the ISS-containing polynucleotide which is proximately associated with a first antigen. A second antigen may be any antigen other than the first antigen, and can be different antigenic regions from the same polypeptide. A second antigen may be any of the antigens described herein, and the principles of obtaining and/or isolating such antigens likewise apply in the context of "second' antigens. Other examples of second antigens are viral variable polypeptides (which includes variable regions or domains of polypeptides), such as coat proteins, including influenza HA or NA. In embodiments which entail administering second antigen, if a first antigen is a conserved polypeptide, the second antigen is generally a variable polypeptide. For example, an influenza vaccine formulation is administered comprising coat protein(s) and core polypeptide such as NP with an ISS-containing polynucleotide. As another example, an HIV vaccine formulation containing a gp120 polypeptide and core antigen with ISS-containing polynucleotide is administered.

ISS-Antigen

ISS may be administered with first antigen in a number of ways. For embodiments which entail administration of first antigen without administration of second antigen, an ISS-containing polynucleotide and first antigen may be administered spatially proximate with respect to each other, or as an admixture (i.e., in solution). For embodiments which entail administration of a second antigen in addition to a first antigen, an ISS-containing polynucleotide is spatially proximate to the first antigen. As described below, spatial proximation can be accomplished in a number of ways, including conjugation, encapsidation, via affixation to a platform or adsorption onto a surface. Generally, and most preferably, an ISS-containing polynucleotide and first antigen are proximately associated at a distance effective to enhance the immune response generated compared to the administration of the ISS and first antigen as an admixture.

The ISS portion can be coupled with the antigen portion of a conjugate in a variety of ways, including covalent and/or non-covalent interactions.

The link between the portions can be made at the 3' or 5' end of the ISS, or at a suitably modified base at an internal position in the ISS. If the antigen is a peptide and contains a suitable reactive group (e.g., an N-hydroxysuccinimide ester) it can be reacted directly with the $N^4$ amino group of cytosine residues. Depending on the number and location of cytosine residues in the ISS, specific coupling at one or more residues can be achieved.

Alternatively, modified oligonucleosides, such as are known in the art, can be incorporated at either terminus, or at internal positions in the ISS. These can contain blocked functional groups which, when deblocked, are reactive with a variety of functional groups which can be present on, or attached to, the antigen of interest.

Where the antigen is a peptide, this portion of the conjugate can be attached to the 3'-end of the ISS through solid support chemistry. For example, the ISS portion can be added to a polypeptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the ISS can be synthesized such that it is connected to a solid support through a cleavable linker extending from the 3'-end. Upon chemical cleavage of the ISS from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified ISS to amino groups of the peptide can be performed as described in Benoit et al. (1987) *Neuromethods* 6:43-72. Conjugation of the thiol-modified ISS to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide portion of the conjugate can be attached to the 5'-end of the ISS through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinah et al. (1991).

An ISS-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an ISS and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between ISS and antigens can occur through DNA binding motifs of molecules that interact with DNA as their natural ligands. For example, such DNA binding motifs can be found in transcription factors and anti-DNA antibodies.

The linkage of the ISS to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular ISS to a peptide or antigen can be formed in several ways. Where the circular ISS is synthesized using recombinant or chemical methods, a modified nucleoside is suitable. Ruth (1991) in *Oligonucleotides and Analogues: A Practical Approach*, IRL Press. Standard linking technology can then be used to connect the circular ISS to the antigen or other peptide. Goodchild (1990) *Bioconjug. Chem.* 1:165. Where the circular ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An ISS may be proximately associated with an antigen(s) in other ways. In some embodiments, an ISS and antigen are proximately associated by encapsulation. In other embodiments, an ISS and antigen are proximately associated by linkage to a platform molecule. A "platform molecule" (also termed "platform") is a molecule containing sites which allow for attachment of the ISS and antigen(s). In other embodiments, an ISS and antigen are proximately associated by adsorption onto a surface, preferably a carrier particle.

In some embodiments, the methods of the invention employ an encapsulating agent that can maintain the proximate association of the ISS and first antigen until the complex is available to the target (or compositions comprising such encapsulating agents). Preferably, the composition comprising ISS, antigen and encapsulating agent is in the form of adjuvant oil-in-water emulsions, microparticles and/or liposomes. More preferably, adjuvant oil-in-water emulsions, microparticles and/or liposomes encapsulating an ISS-immunomodulatory molecule are in the form of particles from about 0.04 μm to about 100 μm in size, preferably any of the following ranges: from about 0.1 μm to about 20 μm; from about 0.15 μm to about 10 μm; from about 0.05 μm to about 1.00 μm; from about 0.05 μm to about 0.5 μm.

Colloidal dispersion systems, such as microspheres, beads, macromolecular complexes, nanocapsules and lipid-based system, such as oil-in-water emulsions, micelles, mixed micelles and liposomes can provide effective encapsulation of ISS-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an ISS-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809-1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing ISS-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

In embodiments in which an ISS and antigen are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287: 123-128; Borel et al. (1995) *Int. Arch. Allergy Immunol.* 107: 264-267; Borel et al. (1996) *Ann. N.Y. Acad. Sci.* 778:80-87. A platform is multi-valent (i.e., contains more than one binding, or linking, site) to accommodate binding to both an ISS and antigen. Other examples of polymeric platforms are dextran, polyacrylamide, ficoll, carboxymethylcellulose, polyvinyl alcohol, and poly D-glutamic acid/D-lysine.

The principles of using platform molecules are well understood in the art. Generally, a platform contains, or is derivatized to contain, appropriate binding sites for ISS and antigen. In addition, or alternatively, ISS and/or antigen is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 200,000, preferably about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine, (in a ratio of 3:2). Other molecules that may be used are albumin and IgG.

Other platform molecules suitable for use within the present invention are the chemically-defined, non-polymeric valency platform molecules disclosed in U.S. Pat. No. 5,552, 391. Other homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an ISS and antigen to a platform molecule may be effected in any number of ways, typically involving one or more crosslinking agents and functional groups on the antigen and ISS platform and platform molecule. Platforms and ISS and antigen must have appropriate linking groups. Linking groups are added to platforms using standard synthetic chemistry techniques. Linking groups may be added to polypeptide antigens and ISS using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting ISS and antigen to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g. 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an ISS and antigen are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an ISS and antigen may be adsorbed include, but are not limited to, activated carbon particles and protein-ceramic nanoplates.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of an ISS and/or antigen to a surface may occur through non-covalent interactions, including ionic and/or hydrophobic interactions.

In general, characteristics of nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the ISS and/or antigen. Carrier particles with adsorbed ISS and/or antigen may be further coated with other substances. The addition of such other substances may, for example, prolong the half-life of the particles once administered to the subject and/or may target the particles to a specific cell type or tissue, as described herein.

Nanocrystalline surfaces to which an ISS and antigen may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. As described in U.S. Pat. No. 5,460,831, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 μm, that carry an inner layer of ISS and an outer layer of antigen.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Polypeptides may also be adsorbed to polyalkylcyanoacrylate nanoparticles. See, for example, Douglas et al., 1987; Schroeder et al. (1998) *Peptides* 19:777-780.

Another adsorbent surface are nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

Administration and Assessment of the Immune Response

The ISS-containing polynucleotide and first antigen can be administered in combination with other pharmaceutical and/or immunogenic and/or immunostimulatory agents and can be combined with a physiologically acceptable carrier thereof. The effective amount and method of administration of the particular ISS-first antigen formulation can vary based on the individual, what condition is to be treated and other factors evident to one skilled in the art. A suitable dosage range is one that provides the desired modulation of immune response to second antigen. Generally, if the ISS-containing polynucleotide and first antigen are administered in proximate association to each other (such as in a conjugate form), a dosage range of the ISS-antigen composition may be, for example, from about any of the following: 1 to 500 µg, 100 to 400 µg, 200 to 300 µg, 1 to 100 µg, 100 to 200 µg, 300 to 400 µg, 400 to 500 µg. In these compositions, the molar ratio of ISS-containing polynucleotide to antigen may vary. If the ISS-containing polynucleotide and first antigen are not proximately associated, i.e., administered as an admixture, generally the dosage ranges are higher, such as, for the ISS-containing polynucleotide, for example, from about any of the following: 10 to 10,000 µg, 2000 to 8000 µg, 4000 to 6000 µg, 10 to 500 µg, 500 to 1000 µg, 1000 to 2000 µg, 2000 to 3000 µg, 6000 to 7000 µg, 7000 to 8000 µg, 8000 to 9000 µg, 9000 to 10,000 µg; and for the first antigen, for example, from about any of the following: 0.1 to 500 µg, 1.0 to 100 µg, 5 to 50 µg, 0.1 to 1.0 µg, 1.0 to 10 µg, 50 to 200 µg, 200 to 400 µg, 300 to 500 µg. The absolute amount given to each patient depends on pharmacological properties such as bioavailability, clearance rate and route of administration.

Timing of Administration and Exposure to Second Antigen

Timing of administration and exposure to second antigen encompasses several aspects: first, timing of administration of ISS-containing polynucleotide with respect to first antigen (i.e., whether the first antigen and ISS-containing polynucleotide are administered together or separately); second, timing of administration of ISS-containing polynucleotide and first antigen with respect to exposure to the second antigen; third, timing of exposure of the second antigen with respect to exposure to first antigen; fourth, for those embodiments in which the second antigen is administered with the first antigen, timing of administration of first antigen with respect to second antigen.

Regarding timing of administration of ISS with respect to first antigen, ISS is preferably administered at the same time as administration of first antigen (i.e., is co-administered). Co-administration can occur as a result of administering an admixture of ISS-containing polynucleotide and first antigen or administering ISS-containing polynucleotide in proximate association with first antigen. However, it is contemplated that ISS and first antigen may also be administered within about any of the following (with respect to each other): 14 days, 12 days, 10 days, 7 days, 5 days, 3 days, 2 days, 1 day, 20 hours, 15 hours, 10 hours, 8 hours, 5 hours, 3 hours, 2 hours, 1 hour, 30 minutes, 15 minutes. If ISS and first antigen are not co-administered, preferably ISS is administered before administration of first antigen. The principles described in this paragraph also apply to timing of administering second antigen in addition to first antigen; thus, the second antigen may be administered within about any of the above times and, in addition, within about any of the following times: 3 weeks, 4 weeks, 6 weeks.

Regarding timing of administering ISS-containing polynucleotide and first antigen with respect to exposure to second antigen, generally, ISS and first antigen are administered either before, during or after exposure to second antigen. If administered before exposure to second antigen, the ISS and first antigen should be administered at an appropriate time before exposure, that is, administration should occur such that the immunomodulation will occur upon exposure to the second antigen. The timing of administration can be determined empirically, for example by measuring any suitable indicia of an antigen-specific immune response as described herein.

Administration of ISS-containing polynucleotide and first antigen occurs at any of various times before exposure to the second antigen, as well as simultaneously with exposure to second antigen. Administration may occur less than about any one or more of the following (with respect to exposure to second antigen): 1 day, 2 days, 3 days, 1 week, 10 days, 2 weeks, 3 weeks, 1 month, 6 weeks, 2 months, 10 weeks, 3 months, 6 months. Additionally, administration may occur more than (at least) about any one or more of the following (with respect to exposure to second antigen): 1 day, 2 days, 3 days, 1 week, 10 days, 2 weeks, 3 weeks, 1 month, 6 weeks, 2 months, 10 weeks, 3 months, 6 months, 1 year, 2 years, 5 years. Administration may consist of one or more doses, at various times. In some embodiments, exposure to second antigen may be at least about any of 1 year, 2 years, 3 years, 5 years, and/or 10 years after administration of ISS-containing polynucleotide and first antigen.

For those embodiments which do not entail administration of a second antigen (and thus require concurrent exposure to first and second antigen), a second antigen may be encountered within a number of hours, days, or even weeks of encountering the first antigen. Accordingly, the first and second antigens may be encountered within about any of the following (with respect to each other): 30 minutes, 1 hour, 2 hours, 5 hours, 12 hours, 20 hours, 24 hours, 2 days, 5 days, 7 days, 10 days, 14 days, 20 days.

Formulations and Routes of Administration

Compositions suitable for topical application may be used, including, but not limited to, physiologically acceptable ointments, creams, rinses, sprays and gels. Topical administration is, for instance, by a dressing or bandage having dispersed therein a delivery system, or by direct administration of a delivery system into incisions or open wounds. Creams, rinses, gels or ointments having dispersed therein an ISS-containing composition are suitable for use as topical ointments or wound filling agents.

ISS and first antigen (with or without second antigen) can be administered in conjunction with one or more immunomodulatory facilitators. The ISS and facilitator can be administered in proximate association, such as an ISS-facilitator conjugate and/or they can be co-administered as a complex in the form of an admixture, such as in an emulsion. Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

Among suitable immunomodulatory cytokine peptides for administration with ISS are the interleukins (e.g., IL-1, IL-2, IL-3, etc.), interferons (e.g., IFN-α, IFN-β, IFN-γ), erythropoietin, colony stimulating factors (e.g., G-CSF, M-CSF, GM-CSF) and TNF-α. Preferably, immunostimulatory peptides for use in conjunction with ISS oligonucleotides are those that stimulate Th1-type immune responses, such as IL-12 (Bliss et al. (1996) *J. Immunol.* 156:887-894), IL-18, TNF-α, β and γ, and/or transforming growth factor (TGF)-α.

Peptides administered with ISS can also include amino acid sequences that mediate protein binding to a specific receptor or that mediate targeting to a specific cell type or tissue. Examples include, but are not limited to, antibodies or antibody fragments, peptide hormones such as human growth hormone, and enzymes. Immunomodulatory peptides also include peptide hormones, peptide neurotransmitters and peptide growth factors. Co-stimulatory molecules such as B7 (CD80), trans-activating proteins such as transcription factors, chemokines such as macrophage chemotactic protein (MCP) and other chemoattractant or chemotactic peptides are also useful peptides for administration with ISS.

An ISS-containing polynucleotide may also be administered in conjunction with an adjuvant. Administration of an antigen with an ISS and an adjuvant leads to a potentiation of a immune response to the antigen and thus, can result in an enhanced immune response compared to that which results from a composition comprising the ISS and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873-875, as well as, lipid-based adjuvants and others described herein. For veterinary use and for production of antibodies in animals, mitogenic components of Freund's adjuvant (both complete and incomplete) can be used.

As with all immunogenic compositions, the immunologically effective amounts of the components must be determined empirically. Factors to be considered include the antigenicity, whether or not ISS and/or antigen will be complexed with or covalently attached to an immunomodulatory facilitator, an adjuvant or carrier protein or other carrier, route of administration and the number of immunizing doses to be administered. Such factors are known in the vaccine art and it is well within the skill in the art to make such determinations.

The route(s) of administration useful in a particular application are apparent to one of skill in the art. Routes of ISS and/or antigen administration include but are not limited to topical, dermal, transdermal, transmucosal, epidermal parenteral, gastrointestinal, and naso-pharyngeal and pulmonary, including transbronchial and transalveolar.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the ISS/antigen-containing composition to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up ISS-containing compositions transferred from the end of the tines. For example, the MONO-VACC old tuberculin test manufactured by Pasteur Merieux of Lyon, France contains a device suitable for introduction of ISS-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of ISS/antigen-containing composition. Use of the device is preferably according to the manufacturer's written instructions included with the device product. Similar devices which can also be used in this embodiment are those which are currently used to perform allergy tests.

Another suitable approach to epidermal administration of ISS is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The ISS can be suspended in a carrier which also contains the chemical irritant or coadministered therewith.

Another delivery method for administering ISS-containing compositions makes use of non-lipid polymers, such as a synthetic polycationic amino polymer. Leff (1997) *Bioworld* 86:1-2.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited to, pharmaceutically acceptable sterile isotonic solutions. Such solutions include, but are not limited to, saline and phosphate buffered saline for injection of the ISS-containing compositions.

Gastrointestinal routes of administration include, but are not limited to, ingestion and rectal. The invention includes ISS-containing compositions suitable for gastrointestinal administration including, but not limited to, pharmaceutically acceptable, powders, pills or liquids for ingestion and suppositories for rectal administration.

Naso-pharyngeal and pulmonary routes of administration include, but are not limited to, inhalation, transbronchial and transalveolar routes. The invention includes ISS-containing compositions suitable for administration by inhalation including, but not limited to, various types of aerosols for inhalation, as well as powder forms for delivery systems. Devices suitable for administration by inhalation of ISS-containing compositions include, but are not limited to, atomizers and vaporizers. Atomizers and vaporizers filled with the powders are among a variety of devices suitable for use in inhalation delivery of powders.

The methods of producing suitable devices for injection, topical application, atomizers and vaporizers are known in the art and will not be described in detail.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the antigen and/or ISS-containing compositions of the invention. The methods of producing the various compositions and devices are within the ability of one skilled in the art and are not described in detail here.

Assessing Modulation of the Immune Response

Analysis (both qualitative and quantitative) of the immune response to ISS/antigen-containing compositions and to the second antigen or second antigen containing compositions can be by any method known in the art, including, but not limited to, measuring antigen-specific antibody production, activation of specific populations of lymphocytes such as $CD4^+$ T cells or NK cells, and/or production of cytokines such as IFN, IL-2, IL-4, or IL-12. Methods for measuring specific antibody responses include enzyme-linked immunosorbent assay (ELISA) and are well known in the art. Measurement of numbers of specific types of lymphocytes such as $CD4^+$ T cells can be achieved, for example, with fluorescence-activated cell sorting (FACS). Cytotoxicity assays can be performed for instance as described in Raz et al. (1994) *Proc. Natl. Acad. Sci. USA* 91:9519-9523. Serum concentrations of cytokines can be measured, for example, by ELISA. These and other assays to evaluate the immune response to an immunogen are well known in the art. See, for example, *Selected Methods in Cellular Immunology* (1980) Mishell and Shiigi, eds., W.H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with ISS as compared to those treated without ISS. Methods to determine the cytokine production of cells include those methods described herein and any known in the art. The type of cytokines produced in response to ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with an ISS/antigen-containing composition and with a second antigen or second antigen containing composition and can be determined by any method known in the art including, but not limited to: (1) a reduction in levels of IL-4 measured before and after antigen-challenge; or detection of lower (or even absent) levels of IL-4 in an ISS-antigen treated and second antigen treated host as compared to an antigen-primed, or primed and challenged, control treated without ISS; (2) an increase in levels of IL-12, IL-18 and/or IFN (α, β or γ) before and after antigen challenge; or detection of higher levels of IL-12, IL-18 and/or IFN (α, β or γ) in an ISS-antigen treated and second antigen treated host as compared to an antigen-primed or, primed and challenged, control treated without ISS; (3) IgG2a antibody production in an ISS-antigen treated and second antigen treated host as compared to a control treated without ISS; and/or (4) a reduction in levels of antigen-specific IgE as measured before and after antigen challenge; or detection of lower (or even absent) levels of antigen-specific IgE in an ISS-antigen treated and second antigen treated host as compared to an antigen-primed, or primed and challenged, control treated without ISS. A variety of these determinations can be made by measuring cytokines made by APCs and/or lymphocytes, preferably macrophages and/or T cells, in vitro or ex vivo using methods described herein or any known in the art. Methods to determine antibody production include any known in the art.

The Th1-type biased cytokine induction which occurs as a result of ISS administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-5, as well as IgE reduction.

Compositions of the Invention

The invention provides compositions comprising an immunomodulatory polynucleotide comprising an ISS and a carrier molecule. The compositions may further comprise an antigen (other than the carrier molecule) and/or a pharmaceutically acceptable excipient. Examples of carriers are provided above.

The invention also provides compositions comprising an immunomodulatory polynucleotide comprising an ISS-containing polynucleotide proximately associated with a first antigen, and further comprising a second antigen. First and second antigens have been described. As an example, in one embodiment, the first antigen is a conserved polypeptide and the second antigen is a variable polypeptide. One or more additional antigens may also be included in these compositions. In one embodiment, the first antigen is a viral conserved polypeptide, such as influenza NP (or an antigenic fragment of NP), and the second antigen is a viral coat polypeptide, such as influenza coat polypeptide (or an antigenic fragment thereof). These compositions, which generally contain an amount sufficient to elicit an antigen-specific immune response upon exposure to second antigen, may also comprise a pharmaceutically acceptable excipient and/or adjuvant.

The following examples are provided to illustrate, but not limit, the invention.

EXAMPLES

Example 1

Effects of ISS+Antigen Co-Administration on Immune Responses to Unrelated Antigens Experiments were performed in BALB/c mice to examine the effects of immunization of an Amb a 1-ISS conjugate (denoted "AIC"; the ISS-containing polynucleotide is 5'-TGACTGTGAACGTTCGAGATGA-3' (SEQ ID NO:1)) on immune responses to unrelated antigens or to non-specific mitogens. The first experiment demonstrated that co-administration of AIC shifts immune responses to the unrelated antigen β-galactosidase (βgal) toward a Th1-type response. The second experiment demonstrated that these effects of AIC on immune responses to βgal were diminished or absent if βgal was delivered four or eight weeks after AIC. The third experiment demonstrated that AIC delivered at the same time but at a different location than the delivery of βgal did not result in a Th-1 type response to the βgal.

Co-Administration of AIC Shifts Immune Responses to βGal Toward Th1

Mice were immunized intradermally (ID) three times at two-week intervals with either 1 μg βgal, 1 μg βgal mixed with 1 μg AIC, or 1 μg βgal mixed with 10 μg AIC. Two weeks after the second and third immunizations, βgal-specific IgG1 and IgG2a responses were determined by ELISA as described in Raz et al. (1996) and Sato et al. (1996), and in the following Example.

The results of such an experiment are shown in FIG. 1 and Table 2 (single asterisk indicates p<0.05 compared to β-gal alone; double asterisk indicates p<0.005 compared to β-gal alone; data shown as mean±standard deviation). After both the second and third immunizations, the antibody response to βgal alone was predominantly an IgG1 response, consistent with a Th2-type response. Co-administration of one or ten μg AIC with βgal significantly increased the IgG2a response to βgal after both the second and third immunization when compared to the IgG2a response seen with βgal alone, consistent with a Th1-type response. Co-administration of 1 μg or 10 μg AIC with βgal also reduced the anti-βgal IgG1 responses when compared to the response with βgal alone.

Four weeks after the third immunization, mice were sacrificed, and spleen cell IFNγ and IL-5 responses to βgal were determined by ELISA. Generally, to measure cytokine secretion, splenocytes are harvested and resuspended in RP10 medium at $5 \times 10^5$ splenocytes per well in 96 well flat-bottomed tissue culture microtiter plates. Culture medium alone as control or βgal is added to triplicate wells. Culture supernatants are sampled at 48 and 72 hours and then analyzed by ELISA for cytokine levels.

The results are shown in Table 3 (single asterisk indicates p<0.05 compared to βgal alone; double asterisk indicates p<0.005 compared to βgal alone; values are provided as mean±standard deviation, 5 spleen pools per group). Spleen cells from mice immunized with βgal alone secreted very little IFNγ and relatively high levels of IL-5 in response to βgal. These responses indicate a Th2-type response and are consistent with the antibody responses discussed above. Co-administration of βgal with 1 or 10 μg of AIC significantly increased the βgal specific IFNγ responses and decreased the βgal-specific IL-5 responses by the spleen cells, again demonstrating a shift of the immune response to βgal in a Th1 direction.

TABLE 3

IFNγ and IL-5 secreted by spleen cells in response to βgal

| Group | IFNγ (pg/ml) | | IL-5 (pg/ml) | |
|---|---|---|---|---|
| | βgal 25 μg/ml | Media Alone | βgal 25 μg/ml | Media Alone |
| βgal (1 μg) + AIC (1 μg) | 469* ± 269 | 72 ± 19 | 136** ± 134 | <32 ± — |
| βgal (1 μg) + AIC (10 μg) | 778** ± 300 | 77 ± 33 | <32** ± — | <32 ± — |
| βgal (1 μg) alone | 191 ± 119 | <62 ± — | 606 ± 338 | <32 ± — |

The results from this experiment demonstrate that co-administration of AIC with an unrelated antigen that normally gives a Th2-type response can significantly modulate the response to that antigen in a Th1-type direction.

The effects of AIC co-administration with βgal on anti-βgal immune responses were statistically significant. For example, the IFNγ responses to βgal were increased four-fold by co-administration of AIC with βgal. By comparison, administration of AIC increased IFNγ responses by 26 to 90-fold compared to administration of Amb a 1 alone.

AIC Delivered Four and Eight Weeks Before βgal has Little Effect on Immune Responses to βgal In this experiment, mice (ten per group) were first immunized ID, twice at a two week intervals with 10 μg AIC. Two

TABLE 2

Effects of AIC co-administration on antibody responses to βgal

| Group | Post 2nd Immunization Anti-βgal Titers | | Post 3rd Immunization Anti-βgal Titers | |
|---|---|---|---|---|
| (dose) | IgG1 | IgG2a | IgG1 | IgG2a |
| βgal (1 μg) + AIC (1 μg) | 2401** ± 1936 | 5228* ± 7497 | 24600** ± 19840 | 30221* ± 41638 |
| βgal (1 μg) + AIC (10 μg) | 7450* ± 7834 | 7065** ± 8464 | 59058 ± 33534 | 49515** ± 21507 |
| βgal (1 μg) alone | 18875 ± 15276 | 776 ± 1241 | 88405 ± 34327 | 7840 ± 8652 | separate lots of AIC induced similar anti-Amb a 1 IgG1 and IgG2a titers (see Table 4; titers <120 were given a value of 120 for calculations; single asterisk indicates p<0.05 compared to the AIC naïve group; data shown as mean±standard deviation). Four or eight weeks after the second AIC dose, an immunization regimen with βgal was begun. Three 1 µg doses of βgal were administered ID every two weeks at the same injection site as the AIC injection site. Mice originally receiving AIC lot "A" were immunized with βgal starting four weeks after the second AIC immunization and mice originally receiving AIC lot "B" were immunized with βgal starting eight weeks after the second AIC immunization. Each βgal immunization regimen included a control group of naïve mice that had not previously been exposed to AIC or βgal. Two weeks after each βgal immunization, mice were bled and βgal-specific IgG1 and IgG2a responses were determined. The results are shown in Table 4. The data demonstrate that exposure to AIC four or eight weeks before immunization with βgal had no significant effect on the IgG1 or IgG2a responses to βgal when delivered at the same site. Immunization with AIC lot "B" did show a significant increase in IgG1 response to subsequent βgal immunization, but this increase was less than two-fold and was seen after the eight week rest but not after the four week rest.

TABLE 4

Effect of previous immunization with AIC on antibody responses to βgal

| Immunization Materials | Anti-Amb a 1 Titers | | | | Anti-β-gal Titers | | | | | |
|---|---|---|---|---|---|---|---|---|---|---|
| | Post 1st AIC | | Post 2nd AIC | | Post 1st β-gal | | Post 2nd β-gal | | Post 3rd β-gal | |
| | IgG1 | IgG2a | IgG1 | IgG2a | IgG1 | IgG2a | IgG1 | IgG2a | IgG1 | IgG2a |
| AIC 10 µg βgal 1 µg 4 weeks post last AIC (lot "A") | 303 ± 377 | 6917 ± 2825 | 90307 ± 55699 | 351316 ± 161276 | 26413 ± 18645 | 723 ± 717 | 140106 ± 117783 | 11708 ± 7286 | 203103 ± 106489 | 46156 ± 54214 |
| βgal 1 µg No AIC | Not tested | Not tested | Not tested | Not tested | 50745 ± 45982 | 1152 ± 1957 | 216887 ± 87938 | 24552 ± 46992 | 238867 ± 99201 | 34323 ± 39687 |
| AIC 10 µg βgal 1 µg 8 weeks post last AIC (lot "B") | 344 ± 212 | 5462 ± 2985 | 77840 ± 45790 | 325703 ± 189856 | 28612 ± 29004 | 588 ± 695 | 113689 ± 70880 | 2264 ± 2713 | 310363* ± 123199 | 12918 ± 13112 |
| βgal 1 µg No AIC | Not tested | Not tested | Not tested | Not tested | 40242 ± 16079 | 559 ± 1004 | 141627 ± 85399 | 1457 ± 1628 | 186913 ± 94555 | 3715 ± 2547 |

Four weeks after the third βgal immunization, mice were sacrificed, spleens were harvested, and spleen cell cultures were stimulated for 4 days in vitro with βgal, as described above. IFNγ and IL-5 levels in culture media were measured by ELISA. The results are shown in Table 5 (data shown as mean±standard deviation). Again, exposure to AIC four or eight weeks before βgal had no significant effect on the cytokine response of spleen cells to βgal.

TABLE 5

Effect of previous immunization with AIC on spleen cell IFNγ and IL-5 responses to βgal

| Immunization Group | IFNγ (pg/ml)$^a$ Stimulated with | | | IL-5 (pg/ml) Stimulated with | | |
|---|---|---|---|---|---|---|
| | β-gal 25 µg/ml | Amb a 1 25 µg/ml | Media Alone | β-gal 25 µg/ml | Amb a 1 25 µg/ml | Media Alone |
| A/C 10 µg βgal 1 µg 4 weeks post last AIC | 1433 ± 920 | 8255 ± 6146 | 332 ± 161 | 1095 ± 870 | 69 ± 69 | <32 ± — |
| βgal 1 µg AIC Naïve | 1080 ± 672 | Not tested | 945 ± 1117 | 1342 ± 926 | Not tested | 96 ± 180 |
| AIC 10 µg βgal 1 µg 8 weeks post last AIC | 2582 ± 1137 | 11535 ± 5040 | 595 ± 429 | 2479 ± 1298 | 184 ± 107 | <32 ± — |
| βgal 1 µg AIC Naïve | 1799 ± 992 | Not tested | 957 ± 680 | 2367 ± 1880 | Not tested | 56 ± 63 |

This experiment demonstrates that while co-administration of AIC with βgal did have a significant effect on the quality of the immune response to βgal, this effect was not observed four or eight weeks after administration of AIC. AIC immunization four or eight weeks earlier had no significant effect on the immune response to subsequent βgal immunization as measured by antibody or cytokine responses.

AIC Delivered at the Same Time but at a Different Site has Little Effect on the Immune Response to βgal In this experiment, the anti-βgal IgG1 and IgG2a responses were compared in groups of ten mice immunized with βgal alone (intramuscularly (IM) in the thigh or ID in the tail), βgal co-administered with 1 or 10 μg of AIC at the same site (IM, thigh or ID, tail), or βgal delivered at one site (IM, thigh) and 1 or 10 μg of AIC delivered at a distant site (ID, tail). One μg doses of βgal were used throughout this experiment. All animals received two injections of the immunogens at a two week interval. Two weeks after each injection, animals were bled and anti-βgal IgG1 and IgG2a titers were determined by ELISA. The results are shown in Table 6 (data shown as mean±standard deviation; single asterisk indicates p<0.05 compared to Amb a 1 by the appropriate route; double asterisk indicates p<0.005 compared to Amb a 1 by the appropriate route).

AIC at either dose had little effect (three-fold or less) on anti-βgal IgG1 responses.

In this experiment, co-delivery of AIC and an unrelated antigen to the same site dramatically increased the Th1 immune response to the unrelated antigen, while delivery of AIC to a site distant from the unrelated antigen had little effect on the Th1 response to that antigen.

Example 2

Administration of ISS with Influenza Nucleoprotein (NP)

Conjugation of Oligonucleotide with Influenza NP Protein and NP Peptide

Influenza NP is prepared from purified influenza virus (such as A/Taiwan/86, H1N1) as described in, for example, Albo et al. (1995) *J. Virol.* 69:3799-3806 and Cooper et al. (1996) *J. Inf. Diseases* 173:279-284). Purified influenza virus (such as A/Taiwan/86, H1N1) is purchased from Research Diagnostics (Flanders, N.J.).

A synthetic peptide for use in ISS conjugates represents amino acids 206-229 of influenza NP and is prepared by standard solid-phase chemistry. This peptide contains a

TABLE 6

Effects of AIC delivered at a separate site on immune responses to βgal

| | Anti-β-gal Titers | | | |
| --- | --- | --- | --- | --- |
| | Post 1st | | Post 2nd | |
| Immunization Materials | 1gG1 | 1gG2a | 1gG1 | 1gG2a |
| AIC 1 μg ID: βgal 1 μg IM | 4060 ± 4717 | 353 ± 514 | 44538 ± 54492 | 3723 ± 6171 |
| AIC 10 μg ID: βgal 1 μg IM | 1747 ± 2549 | 429 ± 872 | 86630 ± 78519 | 10438* ± 17436 |
| AIC 1 μg + βgal 1 μg co-administered IM | 2740 ± 1215 | 3711** ± 2895 | 51055 ± 34682 | 20909** ± 17983 |
| AIC 10 μg + βgal 1 μg co-administered IM | 3144 ± 3201 | 24106* ± 13343 | 84608 ± 68179 | 139930** ± 79117 |
| βgal 1 μg IM | 5959 ± 5686 | 151 ± 182 | 60149 ± 63204 | 2575 ± 4521 |

Immunization of mice with βgal alone by IM injection resulted in relatively high IgG1 responses and relatively low IgG2a responses, consistent with experiments described above and representative of a Th2-type immune response. When βgal was co-administered with AIC (1 or 10 μg) IM, large increases in the anti-βgal IgG2a response was seen, consistent with the experiment described above. After the first immunization, co-administration of 1 μg AIC increased anti-βgal IgG2a responses by 25-fold compared to βgal alone. Co-administration of 10 μg AIC increased IgG2a responses 159-fold. After the second immunization, co-administration of 1 μg AIC with 1 μg βgal increased anti-βgal IgG2a responses by 8-fold. Co-administration of 10 μg AIC with βgal increased IgG2a responses 54-fold. These differences are highly statistically significant (p<0.005).

In contrast to co-administration at the same site, delivery of AIC at a distant site had little effect on anti-βgal IgG2a responses. Same day injection of 1 μg AIC ID in the tail and 1 μg βgal IM in the thigh increased anti-βgal IgG2a responses only 2.3 fold after the first immunization and 1.4 fold after the second, compared to administration of βgal alone. Similarly, using 10 μg AIC at the distant site increased anti-βgal responses only 2.8-fold after the first immunization and only 4-fold (although statistically significant, p<0.05) after the second compared to βgal alone.

strong, conserved T helper cell (Th) epitope that is recognized by BALB/c mice (Gao et al. (1989) *J. Immunol.* 143:3007-3014). This epitope is the most commonly recognized NP epitope in human subjects, with 48% of individuals showing helper T cell recognition (Brett et al. (1991) *J. Immunol.* 147:984-991). This epitope has demonstrated only one amino acid change (at positions 218) in influenza isolates between 1934 and 1975, and no amino acid changes from 1975 through 1990 across H1N1, H2N2 and H3N2 strains (Shu et al. (1993) J. Virol. 67:2723-2729).

Synthetic peptides such as NP 206-229 (FWRGENGRK-TRSAYERMCNILKGK (SEQ ID NO:9)), NP 147-155 (TYQRTRALV (SEQ ID NO:10)), HA 111-119 (FERFE-IFPK (SEQ ID NO:11)) and HA 533-541 (IYSTVASSL (SEQ ID NO:12)) are purchased from Applied Biosystems (Foster City, Calif.). NP 206-219 represents a NP H-$2^d$ Th epitope described above. NP 147-155 represents a conserved NP H-$2^d$ CTL epitope that showed no variation in influenza isolates from 1934 through 1990 (Fu et al. (1997) *J. Virol.* 71:2715-2721). HA 111-119 represents an HA H-$2^d$ Th epitope conserved across all H1N1 strains (Hackett et al. (1983) *J. Exp. Med.* 158:294-302). HA 533-541 represents an HA H-$2^d$ CTL epitope that is found in H1N1 and H2N2 strains (Tamura et al. (1998) *J. Virol.* 72:9404-9406).

5' Thio phosphorothioate ISS oligonucleotides are conjugated to lysine ε-amino groups of both NP and NP peptide using the heterobifunctional cross-linking agent sulfo-SMCC (sulfosuccinimidyl 4-[N-maleimidomethyl]-cyclohexane-1-carboxylate) by the following technique. Five milligrams of NP (100 nmole) or 5 milligrams of NP peptide (2 μmole) is treated with 30-90 fold excess of NEM (N-ethylmaleimide) and 20-50 fold excess of sulfo-SMCC at room temperature for 2 hours. The maleimido-modified NP or NP peptide is purified from unreacted reagents by gel filtration chromatography on a G-25 desalting column. The ISS oligonucleotide used in the conjugate is 5'-TGACTGTGAACGTTC-GAGATGA-3' (SEQ ID NO:1) (Hybridon Speciality Products). A 5'-disulfide modified ISS oligonucleotide (Glen Research, 5'-disulfide Modifier 6) is reduced to the thiol by treatment with tris(2-carboxyethyl)phosphine (TCEP) in PBS. Following purification by gel filtration chromatography on a G-25 desalting column, 5-20 molar excess of the thiol-activated oligonucleotide is incubated with the maleimido-modified NP or NP peptide at room temperature for three hours. The NP-ISS conjugate or NP peptide-ISS conjugate is purified using gel filtration chromatography.

Identical conjugates are made to NP or NP peptide with a control, non-ISS oligonucleotide.

Successful conjugation of NP or NP peptide to ISS is confirmed by non-reducing SDS-PAGE combined with coomassie blue and oligonucleotide-specific silver staining. Quantitation of the oligonucleotide/protein molar ratio is determined by the ratio of the molar oligonucleotide content divided by the molar protein content. The oligonucleotide content is determined by A260 nm absorbance readings and the protein content is determined by BCA assays.

Immunization and Immune Response

Generally, for these experiments, groups of ten, six to eight week old female BALB/c mice are immunized twice (two week interval) intradermally with 1 μg of either ISS-NP conjugate, ISS mixed with NP in 50 μl saline, ISS-NP peptide conjugate, NP-control oligo conjugate, NP peptide-control oligo conjugate, NP alone in 50 μl saline, NP peptide alone or PBS. Mice are bled every two weeks post-immunization, serum separated and stored at −20° C. for later analysis. At week 6, spleens are harvested and splenocytes prepared. Naïve mice are also included in the experiments. The cytokine secretion profile, antigen-dependent antibody responses and antigen-dependent CTL responses of these mice are tested in vitro.

Antibody Assays

Mice are bled via the sinus orbital at 2 weeks post each immunization. Serum is prepared and assayed for anti-NP or anti-HA isotype response by ELISA. Briefly, Nunc Maxisorp plates are coated with either NP or vaccine material (as HA source) overnight at 4° C. Plates are washed and blocked, then samples loaded, serially diluted and incubated overnight at 4° C. Duplicate samples are assayed on separate plates. Plates are again washed and biotinylated goat anti-mouse isotype-specific detection antibody is loaded. After 1 hour at room temperature, plates are again washed and streptavadin-horse-radish peroxidase (HRP) is loaded into wells. Plates are incubated again for 1 hour at room temperature and then washed. Plates are developed with tetramethyl benzidine (TMB) for 10 minutes at room temperature and color development stopped with 2M $H_2SO_4$. Optical densities are read at 450 nm with background subtraction done at 650 nm. Antibody titers are reported as the reciprocal of the highest dilution giving an $OD_{450}$=0.5.

Cytokine Assays

At 4 weeks post second immunization, spleens are harvested and assayed individually for IFNγ and IL-5 production following in vitro stimulation with either NP protein, NP peptides (such as NP 206-229) or HA peptides (such as HA 111-119 and HA peptides from H1 strains). Briefly, spleens are dissociated through a wire screen, washed and cells counted. $2 \times 10^5$ cells/well are plated into 96-well flat bottom tissue culture plates and NP or HA peptide is added to the media. Plates are incubated for 4 days and supernatants harvested and stored at −80° C. until assayed for cytokines by ELISA. Briefly, Nunc Maxisorp plates are coated with either anti-IFNγ or anti-IL5 monoclonal antibody overnight at 4° C. Plates are washed and blocked, then standards and samples loaded, serially diluted and incubated overnight at 4° C. Duplicate samples are assayed on separate plates. Plates are again washed and biotinylated anti-IFNγ or anti-IL5 (MAbs) are loaded. After 1 hour at room temperature, plates are again washed and streptavadin-HRP is loaded into wells. Plates are incubated again for 1 hour at room temperature and then washed. Plates are developed with TMB for 10 minutes at room temperature and color development stopped with 2M $H_2SO_4$. Optical densities are read at 450 nm with background subtraction done at 650 nm. Cytokine concentration of unknown supernatants are read from the standard curve.

CTL Assays

At 4 weeks post second immunization, spleens are harvested and assayed for cytotoxic activity following in vitro stimulation with peptides specific for CTL epitopes of either NP or HA, such as NP 147-155 or HA 533-541. Briefly, spleens are dissociated through a wire screen, washed and cells counted. $5 \times 10^6$ cells are stimulated with peptide (1 μg/ml) for 1 hour at 37° C. and then washed. Peptide stimulated cells ($1 \times 10^6$ cells/well) and non-stimulated spleen cells ($4 \times 10^6$ cells/well) are plated together into 24-well flat bottom tissue culture plates in media containing Rat T-Stim. Plates are incubated at 37° C. with 7% $CO_2$ for 7 days. Cells are fed on Day 3 and washed and replated on Day 5. On Day 7, target cells (SV Balb) are peptide pulsed, $^{51}Cr$ loaded for 1 hour at 37° C. and then washed. The Day 7 effector cells are counted and plated to achieve various effector:target ratios (60:1, 12:1, 2.4:1). Target cells are plated (5000 cells/well) and incubated at 37° C. for 4 hours. Supernatant from each well is then counted for $^{51}Cr$ release and % lysis is calculated.

Influenza Infection

Infectious influenza virus (mouse adapted), such as A/Taiwan/1/86 (H1N1), is delivered intranasally, dropwise using a micropipettor. For a lethal challenge, the virus is titered to establish an $LD_{50}$ and is delivered in a 50 μl volume. For a sublethal challenge, the virus is titered to a dose that is non-lethal but results in infection of the mouse. After the dose is delivered, the mouse is monitored for the next two weeks to confirm infection. Symptoms of infection include weight loss, decrease in activity and/or scruffy fur.

Enhancement of Th1 Responses to Other Influenza Vaccine Antigens by Co-Injection of NP-ISS Compositions with Influenza Vaccine Groups of fifteen, six to eight week old female BALB/c mice are immunized twice (at a two week interval) intradermally with either NP-ISS conjugate (1 μg)+whole-inactivated influenza vaccine, such as made from A/Taiwan/86 virus, at a dose containing 1 μg HA, NP peptide-ISS conjugate (1 μg)+influenza vaccine, NP (1 μg)+influenza vaccine, NP peptide (1 μg)+influenza vaccine, influenza vaccine mixed with a molar equivalent of ISS oligonucleotide or influenza vaccine alone. Mice are bled every two weeks post-immunization, serum separated and prepared for analysis. At week 6, spleens are harvested from five animals per group and splenocytes prepared. Splenocytes are stimulated in vitro with NP or an HA peptide, such as an HA peptide specific for a Th epitope of H1 strains (such as HA 111-119), then culture supernatants are assayed for IFNγ and IL-5. At the same time point, splenocytes are stimulated with an NP peptide or HA peptide, such as NP 147-155 or an HA peptide that is cross-reactive to H1 and H2 CTL epitopes (such as HA 533-541), then assayed for cytotoxic activity. The remaining animals are challenged intranasally with 5 $LD_{50}$ of influenza virus, such as A/Taiwan/86, and monitored for 14 days for mortality and morbidity (such as weight loss, decrease in activity and/or scruffy coat).

Effect of Pre-Injection of NP-ISS on Th1 Responses to NP and Other Viral Proteins Upon Subsequent Influenza Virus Infection.

Mice receive intradermal immunizations with 1 μg doses of NP-ISS conjugate, NP+ISS mixture, NP peptide-ISS conjugate, NP-control oligo conjugate, NP alone, NP peptide alone or PBS as described above. Mice are bled every two weeks post-immunization, serum separated and stored at −20° C. for later analysis. At week 6, mice are challenged with a sublethal dose of influenza virus, such as A/Taiwan/86, via the nasal route. The rate and severity of infection is monitored as compared to mice not treated with NP/ISS compositions. Mice are bled at week 8 and serum prepared. Antibody isotype responses to NP and HA are assayed. At week 10, spleens are harvested and splenocytes are stimulated in vitro with NP or HA peptides, such as NP 206-229 peptide or HA 111-119 peptide, then culture supernatants are assayed for IFNγ and IL-5 levels. At the same timepoint, splenocytes are stimulated with HA or NP peptides, such as the CTL peptides HA 533-541 or NP 147-155, then assayed for cytotoxic activity.

Although the foregoing invention has been described in some detail by way of illustration and example for purposes of clarity and understanding, it will be apparent to those skilled in the art that certain changes and modifications may be practiced. Therefore, the descriptions and examples should not be construed as limiting the scope of the invention, which is delineated by the appended claims.

What is claimed is:

1. A method of modulating an immune response to a second antigen in an individual, comprising co-administering to the individual
   (i) a complex comprising an immunomodulatory polynucleotide proximately associated with a first antigen by encapsulation, adsorption onto a surface or linkage to a platform molecule, and
   (ii) a second antigen that is not part of the complex,
   wherein the polynucleotide comprises an immunostimulatory sequence (ISS) comprising the sequence 5'-cytosine, guanine-3', wherein the complex and the second antigen are administered at the same site in the individual and at the same time in an amount sufficient to modulate an immune response in the individual to the second antigen.

2. The method of claim 1, wherein the immunomodulatory polynucleotide and first antigen are proximately associated by linkage to a platform molecule.

3. The method of claim 1, wherein the immunomodulatory polynucleotide and first antigen are proximately associated by encapsulation.

4. The method of claim 1, wherein the immunomodulatory polynucleotide and first antigen are are proximately associated by adsorption onto a surface.

5. The method of claim 1, wherein the first antigen is an allergen.

6. The method of claim 1, wherein the first antigen is a conserved polypeptide of a virus.

7. The method of claim 6, wherein the conserved viral polypeptide is influenza nucleocapsid protein.

8. The method of claim 6, wherein the conserved viral polypeptide is human immunodeficiency virus (HIV) gag protein.

9. The method of claim 1, wherein the first antigen is a carrier molecule.

10. The method of claim 9, wherein the carrier molecule is diphtheria toxin mutant (CRM 197).

11. The method of claim 9, wherein the carrier molecule is diphtheria toxoid.

12. The method of claim 1, wherein the first antigen is associated with a carrier molecule.

13. The method of claim 1, wherein the immune response is modulated by stimulating a Th1 response to the second antigen.

14. The method of claim 13, wherein production of Th1-associated antibodies is stimulated.

15. The method of claim 13, wherein interferon gamma production is stimulated.

16. The method of claim 15, wherein the ISS comprises the sequence 5'-TCG-3'.

17. The method of claim 15, wherein the ISS comprises the sequence 5'-purine, purine, C, G, pyrimidine, pyrimidine-3'.

18. The method of claim 17, wherein the ISS comprises the sequence 5'-AACGTT-3'.

19. The method of claim 17, wherein the ISS comprises the sequence 5'-purine, purine, C, G, pyrimidine, pyrimidine, C, C-3'.

20. The method of claim 17, wherein the ISS comprises the sequence 5'-purine, purine, C, G, pyrimidine, pyrimidine, C, G-3'.

21. The method of claim 17, wherein the ISS comprises a sequence selected from the group consisting of AACGTTCC, AACGTTCG, GACGTTCC, and GACGTTCG.

22. The method of claim 20, wherein the ISS comprises the sequence TGACTGTGAACGTTCGAGATGA (SEQ ID NO:1).

23. The method of claim 1, wherein the individual is a mammal.

24. The method of claim 23, wherein the mammal is human.

25. The method of claim 5, wherein the allergen is Amb a I.

26. A method of treating an allergy in an individual, comprising co-administering to the individual
(i) a complex comprising an immunomodulatory polynucleotide proximately associated with a first allergen by encapsulation, adsorption onto a surface or linkage to a platform molecule, and
(ii) a second allergen that is not part of the complex,
wherein the polynucleotide comprises an immunostimulatory sequence (ISS) comprising the sequence 5'-cytosine, guanine-3', wherein the complex and the second allergen are administered at the same site in the individual and at the same time in an amount sufficient to stimulate a Th1 immune response in the individual to the second allergen.

27. The method of claim 26, wherein the first allergen is Amb a I.

28. A method of vaccinating an individual, comprising co-administering to the individual
(i) a complex comprising an immunomodulatory polynucleotide proximately associated with a first antigen by encapsulation, adsorption onto a surface or linkage to a platform molecule, and
(ii) a second antigen that is not part of the complex,
wherein the polynucleotide comprises an immunostimulatory sequence (ISS) comprising the sequence 5'-cytosine, guanine-3', wherein the complex and the second antigen are administered at the same site in the individual and at the same time in an amount sufficient to stimulate an immune response in the individual to the second antigen.

29. The method of claim 28, wherein the first antigen is a conserved polypeptide of a virus.

30. The method of claim 29, wherein the conserved viral polypeptide is influenza nucleocapsid protein.

31. The method of claim 29, wherein the conserved viral polypeptide is human immunodeficiency virus (HIV) gag protein.

32. The method of claim 28, wherein the first antigen is a carrier molecule.

33. The method of claim 32, wherein the carrier molecule is diphtheria toxin mutant (CRM 197).

34. The method of claim 32, wherein the carrier molecule is diphtheria toxoid.

35. The method of claim 28, wherein the first antigen is associated with a carrier molecule.

* * * * *

UNITED STATES PATENT AND TRADEMARK OFFICE
CERTIFICATE OF CORRECTION

PATENT NO. : 8,333,980 B2
APPLICATION NO. : 12/270662
DATED : December 18, 2012
INVENTOR(S) : Gary Van Nest et al.

Page 1 of 3

It is certified that error appears in the above-identified patent and that said Letters Patent is hereby corrected as shown below:

On Title Page 2, Item (56), under "Other Publications", column 1, line 6, delete "at" and insert -- et --, therefor.

On Title Page 2, Item (56), under "Other Publications", column 1, line 6, delete "Infuenza" and insert -- Influenza --, therefor.

On Title Page 2, Item (56), under "Other Publications", column 1, line 9, delete "at" and insert -- et --, therefor.

On Title Page 2, Item (56), under "Other Publications", column 1, line 15, delete "at" and insert -- et --, therefor.

On Title Page 2, Item (56), under "Other Publications", column 1, line 16, delete "at" and insert -- et --, therefor.

On Title Page 2, Item (56), under "Other Publications", column 1, line 21, delete "Colulmn" and insert -- Column --, therefor.

On Title Page 2, Item (56), under "Other Publications", column 1, line 35, delete "Administation" and insert -- Administration --, therefor.

On Title Page 2, Item (56), under "Other Publications", column 2, line 17, delete "Neuraminindase" and insert -- Neuraminidase --, therefor.

On Title Page 2, Item (56), under "Other Publications", column 2, line 26, delete "Attachmentof" and insert -- Attachment Of --, therefor.

On Title Page 2, Item (56), under "Other Publications", column 2, line 47, delete "Dematol." and insert -- Dermatol. --, therefor.

Signed and Sealed this
Twenty-fourth Day of September, 2013

Teresa Stanek Rea
*Deputy Director of the United States Patent and Trademark Office*

CERTIFICATE OF CORRECTION (continued)
U.S. Pat. No. 8,333,980 B2

On Title Page 2, Item (56), under "Other Publications", column 2, line 55, delete "Structual Requiements" and insert -- Structural Requirements --, therefor.

On Title Page 3, Item (56), under "Other Publications", column 1, line 63, delete "Coversion" and insert -- Conversion --, therefor.

On Title Page 3, Item (56), under "Other Publications", column 2, line 17, delete "Magintude" and insert -- Magnitude --, therefor.

On Title Page 3, Item (56), under "Other Publications", column 2, line 27, delete "Activiation" and insert -- Activation --, therefor.

On Title Page 3, Item (56), under "Other Publications", column 2, line 30, delete "Oliqonucleotide" and insert -- Oligonucleotide --, therefor.

In the Drawings:

On Sheet 1, on X axis FIG. 1, line 1, delete "mmunization" and insert -- Immunization --, therefor.

In the Specification:

In column 3, line 32, delete "(1991)" and insert -- (1997) --, therefor.

In column 7, line 20, delete "polypepeptide" and insert -- polypeptide --, therefor.

In column 8, line 33, delete "wheat" and insert -- wheal --, therefor.

In column 8, line 44, delete "31:1111-127." and insert -- 31:111-127. --, therefor.

In column 12, line 16, delete "in in" and insert -- in --, therefor.

In column 12, line 22, delete "know" and insert -- known --, therefor.

In column 12, line 45, delete "phosphoramidiates" and insert -- phosphoramidites --, therefor.

In column 13, line 26, delete "oxopyrolo" and insert -- oxopyrrolo --, therefor.

In column 14, line 44, delete "Amb al" and insert -- Amb a 1 --, therefor.

In columns 17-18, Table 1-continued, line 25, delete "lmmunol," and insert -- Immunol, --, therefor.

In columns 17-18, Table 1-continued, line 44, delete "Penicillinium" and insert -- Penicillium --, therefor.

In column 20, line 12, delete ""second"" and insert -- "second" --, therefor.

CERTIFICATE OF CORRECTION (continued)

In column 24, line 31, delete "Dematol." and insert -- Dermatol. --, therefor.

In column 24, line 67, delete "tetraminobenzene," and insert -- tetraaminobenzene, --, therefor.

In columns 24-25, line 67 and line 1, delete "heptaminobetacyclodextrin," and insert -- heptaaminobetacyclodextrin, --, therefor.

In column 25, line 1, delete "tetraminopentaerythritol," and insert -- tetraaminopentaerythritol, --, therefor.

In column 25, line 48, delete "e.g." and insert -- e.g., --, therefor.

In column 25, line 50, delete "haloaceyl, maleiamide" and insert -- haloacetyl, maleimide --, therefor.

In column 39, line 55, delete "streptavadin" and insert -- streptavidin --, therefor.

In column 40, line 15, delete "streptavadin" and insert -- streptavidin --, therefor.

In the Claims:

In column 45, line 54, in Claim 4, delete "are are" and insert -- are --, therefor.

In column 46, line 43, in Claim 16, delete "claim 15" and insert -- claim 1 --, therefor.

In column 46, line 45, in Claim 17, delete "claim 15" and insert -- claim 1 --, therefor.

In column 46, lines 66-67, in Claim 25, delete "Amb a l" and insert -- Amb a 1 --, therefor.

In column 47, line 17, in Claim 27, delete "Amb a l" and insert -- Amb a 1 --, therefor.